US012747293B2

(12) United States Patent
Gibson et al.

(10) Patent No.: US 12,747,293 B2
(45) Date of Patent: Sep. 29, 2026

(54) MICA/B ANTIBODIES AND METHODS OF USE

(71) Applicant: Cullinan Mica Corporation, Cambridge, MA (US)

(72) Inventors: Neil Gibson, Cambridge, MA (US); Justin Chapman, Cambridge, MA (US); Xin Du, Cambridge, MA (US)

(73) Assignee: Cullinan Mica Corporation, Cambridge, MA (US)

(*) Notice: Subject to any disclaimer, the term of this patent is extended or adjusted under 35 U.S.C. 154(b) by 784 days.

(21) Appl. No.: 18/327,566

(22) Filed: Jun. 1, 2023

(65) Prior Publication Data

US 2024/0067731 A1 Feb. 29, 2024

Related U.S. Application Data

(63) Continuation of application No. 16/938,554, filed on Jul. 24, 2020, now abandoned, which is a continuation of application No. PCT/US2019/015025, filed on Jan. 24, 2019.

(60) Provisional application No. 62/621,892, filed on Jan. 25, 2018.

(51) Int. Cl.

| | |
|---|---|
| ***C07K 16/00*** | (2006.01) |
| ***A61K 39/00*** | (2006.01) |
| ***C07K 16/28*** | (2006.01) |

(52) U.S. Cl.

CPC ...... *C07K 16/2833* (2013.01); *C07K 2317/51* (2013.01); *C07K 2317/515* (2013.01); *C07K 2317/56* (2013.01); *C07K 2317/565* (2013.01); *C07K 2317/73* (2013.01); *C07K 2317/92* (2013.01)

(58) Field of Classification Search

CPC ............ C07K 16/2833; C07K 2317/51; C07K 2317/515; C07K 2317/56; C07K 2317/565; A61P 35/02; A61P 35/00; A61K 2039/505

See application file for complete search history.

(56) References Cited

U.S. PATENT DOCUMENTS

| | | | |
|---|---|---|---|
| 7,771,718 | B2 | 8/2010 | Spies et al. |
| 7,959,916 | B2 | 6/2011 | Spies et al. |
| 10,577,416 | B2 | 3/2020 | Blery et al. |
| 2008/0260727 | A1 | 10/2008 | Lanier et al. |
| 2012/0315287 | A1 | 12/2012 | Wu |
| 2014/0356321 | A1 | 12/2014 | Cheung et al. |
| 2015/0191542 | A1 | 7/2015 | Blery et al. |
| 2015/0210761 | A1 | 7/2015 | Kim et al. |
| 2016/0030659 | A1 | 2/2016 | Cheney |
| 2016/0046689 | A1 | 2/2016 | Cheney |
| 2017/0008962 | A1 | 1/2017 | Wucherpfennig et al. |
| 2017/0121776 | A1 | 5/2017 | Soliman et al. |
| 2017/0198054 | A1 | 7/2017 | Harvey et al. |
| 2018/0154064 | A1 | 6/2018 | Cheney |
| 2019/0315870 | A1 | 10/2019 | Kuhne et al. |
| 2020/0023071 | A1 | 1/2020 | Blery et al. |
| 2020/0055939 | A1 | 2/2020 | Lombana et al. |

FOREIGN PATENT DOCUMENTS

| | | | |
|---|---|---|---|
| EP | 1857116 | A1 | 11/2007 |
| EP | 2970490 | A2 | 1/2016 |
| EP | 3293271 | A1 | 3/2018 |
| EP | 3529280 | A1 | 8/2019 |
| EP | 3532091 | A2 | 9/2019 |
| KR | 1020097020519 | A | 11/2016 |
| WO | 2013049517 | A2 | 4/2013 |
| WO | 2013117647 | A1 | 8/2013 |
| WO | 2014/140904 | A3 | 9/2014 |
| WO | 2014140884 | A2 | 9/2014 |
| WO | 2014140904 | A2 | 9/2014 |
| WO | 2015003114 | A1 | 8/2015 |
| WO | 2016126213 | A1 | 8/2016 |
| WO | 2017/221072 | A2 | 12/2017 |
| WO | 2018/081648 | A2 | 5/2018 |
| WO | 2018141959 | A1 | 8/2018 |
| WO | 2018201051 | A1 | 11/2018 |
| WO | 2019/147863 | A2 | 8/2019 |
| WO | 2019/195409 | A1 | 10/2019 |
| WO | 2020028428 | A2 | 2/2020 |
| WO | 2020035345 | A1 | 2/2020 |

OTHER PUBLICATIONS

Morel et al, Innate Pharma, AACR meeting 2016. (Year: 2016).*
Australian Patent Office, Examination Report, Application No. 2019211411, dated Nov. 19, 2024, 4 pages.
Jinushi et al., "Expression and Role of MICA and MICB in Human Hepatocellular Carcinomas and their Regulation by Retinoic Acid," Int. J. Cancer: 104, 2003, pp. 354-361.
Notification of Transmittal of the International Search Report and the Written Opinion of the International Searching Authority, or the Declaration, mailed Sep. 12, 2019, 17 pages.
Wang et al., "A Bispecific Protein rG7S-MICA Recuits Natural Killer Cells and Enhances NKG2D-Mediated Immunosurveillance Against Helatocellular Carcinoma," Cancer Letters 372 (2016) pp. 166-178.
Canadian Patent Office, "Office Action for Application No. 3,089,478," 7 pages, dated Sep. 20, 2023.

(Continued)

*Primary Examiner* — Lei Yao

(74) *Attorney, Agent, or Firm* — Lathrop GPM LLP; Malaika O.D. Tyson

(57) ABSTRACT

Provided herein are antibodies that specifically bind to MICA/B having variable heavy chain domains (VH), variable light chain domains (VL), and complementarity determining regions disclosed herein, as well as methods and uses thereof.

12 Claims, 4 Drawing Sheets

Specification includes a Sequence Listing.

(56) References Cited

OTHER PUBLICATIONS

IP Australia Patent Office, Office Action No. 2 regarding Application No. 2019211411, dated Oct. 15, 2025.

IP Australia Patent Office, Office Action No. 3 regarding Application No. 2019211411, dated Oct. 23, 2025.

Mexican Institute of Industrial Property, Office Action regarding Application No. MX/a/2020/007880, dated Oct. 16, 2025.

Korean Intellectual Property Office, "Office Action," regarding Application No. 10-2020-7023978, 13 pages, dated Mar. 13, 2024.

Brazilian Patent Office, Preliminary Office Action for Brazilian Patent Application No. BR112020015142-4, mailed Sep. 15, 2025.

Ghadially et al., "MHC class I chain-related protein A and B (MICA and MICB) are predominantly expressed intracellularly in tumour and normal tissue", British J. Cancer, Mar. 23, 2017, 116(9): 1208-1217.

Mexican Patent Office, Office Action for Mexican patent application no. MX/a/2020/007880, mailed May 9, 2025.

Rudikoff et al., "Single amino acid substition altering antigen-binding specificity", PNAS USA, Mar. 1982, 79(6): 1979-1983.

Salih et al., "Release of MICB Molecules by Tumor Cells: Mechanism and Soluble MICB in Sera of Cancer Patients", Human Immunol., Mar. 2006, 67(3): 188-195.

European Patent Office, Supplementary European Search Report for European Application No. EP 19743264.4, mailed Oct. 11, 2021.

Www.bamomab.com/documents/MIC/BAMO1-100, "Anti-Human MICA/B Monoclonal Antibody BAMO1," 1 pg., dated Jan. 1, 2004.

Israel Patent Office, "Office Action," regarding Application No. 276187, 5 pgs., dated Mar. 24, 2024.

* cited by examiner

Analyte: 6xHis-MICA*08

Analyte: 6xHis-MICA*01

| Analyte | KD (M) | kon(1/Ms) | kdis(1/s) | Full R^2 |
|---|---|---|---|---|
| MICA*08 | 2.41E-09 | 2.25E+05 | 4.96E-04 | 9.74E-01 |
| MICA*01 | 3.09E-09 | 1.50E+05 | 4.78E-04 | 9.83E-01 |

MICA/B ANTIBODIES AND METHODS OF USE

CROSS-REFERENCE

This application is a continuation of U.S. application Ser. No. 16/938,554, filed Jul. 24, 2020, which is a continuation of International Application No. PCT/US2019/015025 filed Jan. 24, 2019, which claims the benefit of U.S. Provisional Application No. 62/621,892, filed Jan. 25, 2018, which applications are incorporated herein by reference.

SEQUENCE LISTING

The instant application contains a Sequence Listing which has been submitted in electronic format as an XML file. The Sequence Listing is provided as an XML file entitled C2000-702021 SL, created on May 31, 2023, which is 15,783 bytes in size. The Sequence Listing is incorporated herein by reference in its entirety.

SUMMARY

Disclosed herein, are monoclonal antibodies that specifically bind to MICA/B and thereby modulating an immune response against disease cells.

Disclosed herein, in certain embodiments, are monoclonal antibodies or an antigen-binding fragments thereof, comprising a light chain variable domain (VL) comprising an amino acid sequence at least 80% identical an amino acid sequence set forth as SEQ ID NO: 7. Disclosed herein, in certain embodiments, are monoclonal antibodies or an antigen-binding fragments thereof, comprising a light chain variable domain (VL) comprising an amino acid sequence at least 90% identical an amino acid sequence set forth as SEQ ID NO: 7. Disclosed herein, in certain embodiments, are monoclonal antibodies or an antigen-binding fragments thereof, comprising a light chain variable domain (VL) comprising an amino acid sequence at least 95% identical an amino acid sequence set forth as SEQ ID NO: 7. Disclosed herein, in certain embodiments, are monoclonal antibodies or an antigen-binding fragments thereof, comprising a light chain variable domain (VL) comprising an amino acid sequence at least 99% identical an amino acid sequence set forth as SEQ ID NO: 7. Disclosed herein, in certain embodiments, are monoclonal antibodies or an antigen-binding fragments thereof, comprising a light chain variable domain (VL) comprising an amino acid sequence 100% identical an amino acid sequence set forth as SEQ ID NO: 7. Disclosed herein, in certain embodiments, are monoclonal antibodies or an antigen-binding fragments thereof, comprising a light chain variable domain (VL) comprising an amino acid sequence at least 80% identical an amino acid sequence set forth as SEQ ID NO: 7, wherein the monoclonal antibody or antigen-binding fragment thereof comprises a light chain that does not have an amino acid sequence set forth as SEQ ID NO: 9, or wherein the monoclonal antibody or antigen-binding fragment thereof comprises a heavy chain that does not have an amino acid sequence set forth as SEQ ID NO: 10. Disclosed herein, in certain embodiments, are monoclonal antibodies or an antigen-binding fragments thereof, comprising a light chain variable domain (VL) comprising an amino acid sequence at least 90% identical an amino acid sequence set forth as SEQ ID NO: 7, wherein the monoclonal antibody or antigen-binding fragment thereof comprises a light chain that does not have an amino acid sequence set forth as SEQ ID NO: 9, or wherein the monoclonal antibody or antigen-binding fragment thereof comprises a heavy chain that does not have an amino acid sequence set forth as SEQ ID NO: 10. Disclosed herein, in certain embodiments, are monoclonal antibodies or an antigen-binding fragments thereof, comprising a light chain variable domain (VL) comprising an amino acid sequence at least 95% identical an amino acid sequence set forth as SEQ ID NO: 7, wherein the monoclonal antibody or antigen-binding fragment thereof comprises a light chain that does not have an amino acid sequence set forth as SEQ ID NO: 9, or wherein the monoclonal antibody or antigen-binding fragment thereof comprises a heavy chain that does not have an amino acid sequence set forth as SEQ ID NO: 10. Disclosed herein, in certain embodiments, are monoclonal antibodies or an antigen-binding fragments thereof, comprising a light chain variable domain (VL) comprising an amino acid sequence at least 99% identical an amino acid sequence set forth as SEQ ID NO: 7, wherein the monoclonal antibody or antigen-binding fragment thereof comprises a light chain that does not have an amino acid sequence set forth as SEQ ID NO: 9, or wherein the monoclonal antibody or antigen-binding fragment thereof comprises a heavy chain that does not have an amino acid sequence set forth as SEQ ID NO: 10. Disclosed herein, in certain embodiments, are monoclonal antibodies or an antigen-binding fragments thereof, comprising a light chain variable domain (VL) comprising an amino acid sequence 100% identical an amino acid sequence set forth as SEQ ID NO: 7, wherein the monoclonal antibody or antigen-binding fragment thereof comprises a light chain that does not have an amino acid sequence set forth as SEQ ID NO: 9, or wherein the monoclonal antibody or antigen-binding fragment thereof comprises a heavy chain that does not have an amino acid sequence set forth as SEQ ID NO: 10. In some embodiments, the monoclonal antibody or antigen-binding fragment thereof comprises a heavy chain variable domain (VH) comprising an amino acid sequence at least 80% identical to an amino acid sequence set forth as SEQ ID NO: 8. In some embodiments, the monoclonal antibody or antigen-binding fragment thereof comprises a heavy chain variable domain (VH) comprising an amino acid sequence at least 90% identical to an amino acid sequence set forth as SEQ ID NO: 8. In some embodiments, the monoclonal antibody or antigen-binding fragment thereof comprises a heavy chain variable domain (VH) comprising an amino acid sequence at least 95% identical to an amino acid sequence set forth as SEQ ID NO: 8. In some embodiments, the monoclonal antibody or antigen-binding fragment thereof comprises a heavy chain variable domain (VH) comprising an amino acid sequence at least 99% identical to an amino acid sequence set forth as SEQ ID NO: 8. In some embodiments, the monoclonal antibody or antigen-binding fragment thereof comprises a heavy chain variable domain (VH) comprising an amino acid sequence 100% identical to an amino acid sequence set forth as SEQ ID NO: 8. In some embodiments, the light chain comprises an amino acid sequence wherein at least 1 to 10 amino acids of amino acid sequence set forth as SEQ ID NO: 9 are modified. In some embodiments, the heavy chain comprises an amino acid sequence wherein at least 1 to 10 amino acids of amino acid sequence set forth as SEQ ID NO: 10 are modified. In some embodiments, the monoclonal antibody or antigen-binding fragment thereof specifically binds to a MICA protein, a MICB protein, or both MICA and MICB protein. In some embodiments, the monoclonal antibody or antigen-binding fragment thereof binds to an alpha-3 domain of a MICA protein, a MICB protein, or both MICA and MICB protein. In some embodiments, the MICA protein is membrane-bound MICA protein, soluble MICA protein, or both. In some embodiments, the MICB protein is membrane-bound MICB protein, soluble MICB protein, or both. In some embodiments, the monoclonal antibody or antigen-binding fragment thereof is selected from a whole immunoglobulin, an scFv, a Fab, a $F(ab')_2$, or a disulfide linked Fv. In some embodiments, the monoclonal antibody or antigen-binding fragment thereof is an IgG or IgM. In some embodiments, the monoclonal antibody or fragment thereof is humanized or chimeric.

Disclosed herein, in certain embodiments, are monoclonal antibodies or an antigen-binding fragments thereof, comprising a heavy chain variable domain (VH) comprising an amino acid sequence at least 80% identical to an amino acid sequence set forth as SEQ ID NO: 8. Disclosed herein, in certain embodiments, are monoclonal antibodies or an antigen-binding fragments thereof, comprising a heavy chain variable domain (VH) comprising an amino acid sequence at least 90% identical to an amino acid sequence set forth as SEQ ID NO: 8. Disclosed herein, in certain embodiments, are monoclonal antibodies or an antigen-binding fragments thereof, comprising a heavy chain variable domain (VH) comprising an amino acid sequence at least 95% identical to an amino acid sequence set forth as SEQ ID NO: 8. Disclosed herein, in certain embodiments, are monoclonal antibodies or an antigen-binding fragments thereof, comprising a heavy chain variable domain (VH) comprising an amino acid sequence at least 99% identical to an amino acid sequence set forth as SEQ ID NO: 8. Disclosed herein, in certain embodiments, are monoclonal antibodies or an antigen-binding fragments thereof, comprising a heavy chain variable domain (VH) comprising an amino acid sequence 100% identical to an amino acid sequence set forth as SEQ ID NO: 8. Disclosed herein, in certain embodiments, are monoclonal antibodies or an antigen-binding fragments thereof, comprising a heavy chain variable domain (VH) comprising an amino acid sequence at least 80% identical to an amino acid sequence set forth as SEQ ID NO: 8, wherein the monoclonal antibody or antigen-binding fragment thereof comprises a heavy chain that does not have an amino acid sequence set forth as SEQ ID NO: 10, or wherein the monoclonal antibody or antigen-binding fragment thereof comprises a light chain that does not have an amino acid sequence set forth as SEQ ID NO: 9. Disclosed herein, in certain embodiments, are monoclonal antibodies or an antigen-binding fragments thereof, comprising a heavy chain variable domain (VH) comprising an amino acid sequence at least 90% identical to an amino acid sequence set forth as SEQ ID NO: 8, wherein the monoclonal antibody or antigen-binding fragment thereof comprises a heavy chain that does not have an amino acid sequence set forth as SEQ ID NO: 10, or wherein the monoclonal antibody or antigen-binding fragment thereof comprises a light chain that does not have an amino acid sequence set forth as SEQ ID NO: 9. Disclosed herein, in certain embodiments, are monoclonal antibodies or an antigen-binding fragments thereof, comprising a heavy chain variable domain (VH) comprising an amino acid sequence at least 95% identical to an amino acid sequence set forth as SEQ ID NO: 8, wherein the monoclonal antibody or antigen-binding fragment thereof comprises a heavy chain that does not have an amino acid sequence set forth as SEQ ID NO: 10, or wherein the monoclonal antibody or antigen-binding fragment thereof comprises a light chain that does not have an amino acid sequence set forth as SEQ ID NO: 9. Disclosed herein, in certain embodiments, are monoclonal antibodies or an antigen-binding fragments thereof, comprising a heavy chain variable domain (VH) comprising an amino acid sequence at least 99% identical to an amino acid sequence set forth as SEQ ID NO: 8, wherein the monoclonal antibody or antigen-binding fragment thereof comprises a heavy chain that does not have an amino acid sequence set forth as SEQ ID NO: 10, or wherein the monoclonal antibody or antigen-binding fragment thereof comprises a light chain that does not have an amino acid sequence set forth as SEQ ID NO: 9. Disclosed herein, in certain embodiments, are monoclonal antibodies or an antigen-binding fragments thereof, comprising a heavy chain variable domain (VH) comprising an amino acid sequence 100% identical to an amino acid sequence set forth as SEQ ID NO: 8, wherein the monoclonal antibody or antigen-binding fragment thereof comprises a heavy chain that does not have an amino acid sequence set forth as SEQ ID NO: 10, or wherein the monoclonal antibody or antigen-binding fragment thereof comprises a light chain that does not have an amino acid sequence set forth as SEQ ID NO: 9. In some embodiments, the monoclonal antibody or antigen-binding fragment thereof comprises a light chain variable domain (VL) comprising an amino acid sequence at least 80% identical to an amino acid sequence set forth as SEQ ID NO: 7. In some embodiments, the monoclonal antibody or antigen-binding fragment thereof comprises a light chain variable domain (VL) comprising an amino acid sequence at least 90% identical to an amino acid sequence set forth as SEQ ID NO: 7. In some embodiments, the monoclonal antibody or antigen-binding fragment thereof comprises a light chain variable domain (VL) comprising an amino acid sequence at least 95% identical to an amino acid sequence set forth as SEQ ID NO: 7. In some embodiments, the monoclonal antibody or antigen-binding fragment thereof comprises a light chain variable domain (VL) comprising an amino acid sequence at least 99% identical to an amino acid sequence set forth as SEQ ID NO: 7. In some embodiments, the monoclonal antibody or antigen-binding fragment thereof comprises a light chain variable domain (VL) comprising an amino acid sequence 100% identical to an amino acid sequence set forth as SEQ ID NO: 7. In some embodiments, the heavy chain comprises an amino acid sequence wherein at least 1 to 10 amino acids of amino acid sequence set forth as SEQ ID NO: 10 are modified. In some embodiments, the light chain comprises an amino acid sequence wherein at least 1 to 10 amino acids of amino acid sequence set forth as SEQ ID NO: 9 are modified. In some embodiments, the monoclonal antibody or antigen-binding fragment thereof specifically binds to a MICA protein, a MICB protein, or both MICA and MICB protein. In some embodiments, the monoclonal antibody or antigen-binding fragment thereof binds to an alpha-3 domain of a MICA protein, a MICB protein, or both MICA and MICB protein. In some embodiments, the MICA protein is membrane-bound MICA protein, soluble MICA protein, or both. In some embodiments, the MICB protein is membrane-bound MICB protein, soluble MICB protein, or both. In some embodiments, the monoclonal antibody or antigen-binding fragment thereof is selected from a whole immunoglobulin, an scFv, a Fab, a $F(ab')_2$, or a disulfide linked Fv. In some embodiments, the monoclonal antibody or antigen-binding fragment thereof is an IgG or IgM. In some embodiments, the monoclonal antibody or fragment thereof is humanized or chimeric.

Disclosed herein, in certain embodiments, are monoclonal antibodies or an antigen-binding fragments thereof, comprising at least one of a light chain complementarity determining region 1 (CDR1) sequence at least 80% identical to SEQ ID NO: 1, a light chain complementarity determining region 2 (CDR2) sequence at least 80% identical to SEQ ID NO: 2, and a light chain complementarity determining region 3 (CDR3) sequence at least 80% identical to SEQ ID NO: 3. Disclosed herein, in certain embodiments, are monoclonal antibodies or an antigen-binding fragments thereof, comprising at least one of a light chain complementarity determining region 1 (CDR1) sequence at least 90% identical to SEQ ID NO: 1, a light chain complementarity determining region 2 (CDR2) sequence at least 90% identical to SEQ ID NO: 2, and a light chain complementarity determining region 3 (CDR3) sequence at least 90% identical to SEQ ID NO: 3. Disclosed herein, in certain embodiments, are monoclonal antibodies or an antigen-binding fragments thereof, comprising at least one of a light chain complementarity determining region 1 (CDR1) sequence at least 95% identical to SEQ ID NO: 1, a light chain complementarity determining region 2 (CDR2) sequence at least 95% identical to SEQ ID NO: 2, and a light chain complementarity determining region 3 (CDR3) sequence at least 95% identical to SEQ ID NO: 3. Disclosed herein, in certain embodiments, are monoclonal antibodies or an antigen-binding fragments thereof, comprising at least one of a light chain complementarity determining region 1 (CDR1) sequence at least 99% identical to SEQ ID NO: 1, a light chain complementarity determining region 2 (CDR2) sequence at least 99% identical to SEQ ID NO: 2, and a light chain complementarity determining region 3 (CDR3) sequence at least 99% identical to SEQ ID NO: 3. Disclosed herein, in certain embodiments, are monoclonal antibodies or an antigen-binding fragments thereof, comprising at least one of a light chain complementarity determining region 1 (CDR1) sequence at least 100% identical to SEQ ID NO: 1, a light chain complementarity determining region 2 (CDR2) sequence at least 100% identical to SEQ ID NO: 2, and a light chain complementarity determining region 3 (CDR3) sequence at least 100% identical to SEQ ID NO: 3. Disclosed herein, in certain embodiments, are monoclonal antibodies or an antigen-binding fragments thereof, comprising at least one of a light chain complementarity determining region 1 (CDR1) sequence at least 80% identical to SEQ ID NO: 1, a light chain complementarity determining region 2 (CDR2) sequence at least 80% identical to SEQ ID NO: 2, and a light chain complementarity determining region 3 (CDR3) sequence at least 80% identical to SEQ ID NO: 3, wherein the monoclonal antibody or antigen-binding fragment thereof comprises a light chain that does not have an amino acid sequence set forth as SEQ ID NO: 9, or wherein the monoclonal antibody or antigen-binding fragment thereof comprises a heavy chain that does not have an amino acid sequence set forth as SEQ ID NO: 10. Disclosed herein, in certain embodiments, are monoclonal antibodies or an antigen-binding fragments thereof, comprising at least one of a light chain complementarity determining region 1 (CDR1) sequence at least 90% identical to SEQ ID NO: 1, a light chain complementarity determining region 2 (CDR2) sequence at least 90% identical to SEQ ID NO: 2, and a light chain complementarity determining region 3 (CDR3) sequence at least 90% identical to SEQ ID NO: 3, wherein the monoclonal antibody or antigen-binding fragment thereof comprises a light chain that does not have an amino acid sequence set forth as SEQ ID NO: 9, or wherein the monoclonal antibody or antigen-binding fragment thereof comprises a heavy chain that does not have an amino acid sequence set forth as SEQ ID NO: 10. Disclosed herein, in certain embodiments, are monoclonal antibodies or an antigen-binding fragments thereof, comprising at least one of a light chain complementarity determining region 1 (CDR1) sequence at least 95% identical to SEQ ID NO: 1, a light chain complementarity determining region 2 (CDR2) sequence at least 95% identical to SEQ ID NO: 2, and a light chain complementarity determining region 3 (CDR3) sequence at least 95% identical to SEQ ID NO: 3, wherein the monoclonal antibody or antigen-binding fragment thereof comprises a light chain that does not have an amino acid sequence set forth as SEQ ID NO: 9, or wherein the monoclonal antibody or antigen-binding fragment thereof comprises a heavy chain that does not have an amino acid sequence set forth as SEQ ID NO: 10. Disclosed herein, in certain embodiments, are monoclonal antibodies or an antigen-binding fragments thereof, comprising at least one of a light chain complementarity determining region 1 (CDR1) sequence at least 99% identical to SEQ ID NO: 1, a light chain complementarity determining region 2 (CDR2) sequence at least 99% identical to SEQ ID NO: 2, and a light chain complementarity determining region 3 (CDR3) sequence at least 99% identical to SEQ ID NO: 3, wherein the monoclonal antibody or antigen-binding fragment thereof comprises a light chain that does not have an amino acid sequence set forth as SEQ ID NO: 9, or wherein the monoclonal antibody or antigen-binding fragment thereof comprises a heavy chain that does not have an amino acid sequence set forth as SEQ ID NO: 10. Disclosed herein, in certain embodiments, are monoclonal antibodies or an antigen-binding fragments thereof, comprising at least one of a light chain complementarity determining region 1 (CDR1) sequence at least 100% identical to SEQ ID NO: 1, a light chain complementarity determining region 2 (CDR2) sequence at least 100% identical to SEQ ID NO: 2, and a light chain complementarity determining region 3 (CDR3) sequence at least 100% identical to SEQ ID NO: 3, wherein the monoclonal antibody or antigen-binding fragment thereof comprises a light chain that does not have an amino acid sequence set forth as SEQ ID NO: 9, or wherein the monoclonal antibody or antigen-binding fragment thereof comprises a heavy chain that does not have an amino acid sequence set forth as SEQ ID NO: 10. In some embodiments, the monoclonal antibody or antigen-binding fragment thereof comprises at least one of a heavy chain complementarity determining region 1 (CDR1) sequence at least 80% identical to SEQ ID NO: 4, a heavy chain complementarity determining region 2 (CDR2) sequence at least 80% identical to SEQ ID NO: 5, and a heavy chain complementarity determining region 3 (CDR3) sequence at least 80% identical to SEQ ID NO: 6. In some embodiments, the monoclonal antibody or antigen-binding fragment thereof comprises at least one of a heavy chain complementarity determining region 1 (CDR1) sequence at least 90% identical to SEQ ID NO: 4, a heavy chain complementarity determining region 2 (CDR2) sequence at least 90% identical to SEQ ID NO: 5, and a heavy chain complementarity determining region 3 (CDR3) sequence at least 90% identical to SEQ ID NO: 6. In some embodiments, the monoclonal antibody or antigen-binding fragment thereof comprises at least one of a heavy chain complementarity determining region 1 (CDR1) sequence at least 95% identical to SEQ ID NO: 4, a heavy chain complementarity determining region 2 (CDR2) sequence at least 95% identical to SEQ ID NO: 5, and a heavy chain complementarity determining region 3 (CDR3) sequence at least 95% identical to SEQ ID NO: 6. In some embodiments, the monoclonal antibody or antigen-binding fragment thereof comprises at least one of a heavy chain complementarity determining region 1 (CDR1) sequence at least 99% identical to SEQ ID NO: 4, a heavy chain complementarity determining region 2 (CDR2) sequence at least 99% identical to SEQ ID NO: 5, and a heavy chain complementarity determining region 3 (CDR3) sequence at least 99% identical to SEQ ID NO: 6. In some embodiments, the monoclonal antibody or antigen-binding fragment thereof comprises at least one of a heavy chain complementarity determining region 1 (CDR1) sequence 100% identical to SEQ ID NO: 4, a heavy chain complementarity determining region 2 (CDR2) sequence 100% identical to SEQ ID NO: 5, and a heavy chain complementarity determining region 3 (CDR3) sequence 100% identical to SEQ ID NO: 6. In some embodiments, the monoclonal antibody or antigen-binding fragment thereof comprises a light chain variable domain (VL) comprising an amino acid sequence at least 80% identical to an amino acid sequence set forth as SEQ ID NO: 7. In some embodiments, the monoclonal antibody or antigen-binding fragment thereof comprises a heavy chain variable domain (VH) comprising an amino acid sequence at least 80% identical to an amino acid sequence set forth as SEQ ID NO: 8. In some embodiments, the monoclonal antibody or antigen-binding fragment thereof comprises a heavy chain variable domain (VH) comprising an amino acid sequence at least 80% identical to an amino acid sequence set forth as SEQ ID NO: 8. In some embodiments, the monoclonal antibody or antigen-binding fragment thereof comprises a light chain variable domain (VL) comprising an amino acid sequence at least 80% identical to an amino acid sequence set forth as SEQ ID NO: 7. In some embodiments, the light chain comprises an amino acid sequence wherein at least 1 to 10 amino acids of amino acid sequence set forth as SEQ ID NO: 9 are modified. In some embodiments, the heavy chain comprises an amino acid sequence wherein at least 1 to 10 amino acids of amino acid sequence set forth as SEQ ID NO: 10 are modified. In some embodiments, the monoclonal antibody or antigen-binding fragment thereof specifically binds to a MICA protein, a MICB protein, or both MICA and MICB protein. In some embodiments, the monoclonal antibody or antigen-binding fragment thereof binds to an alpha-3 domain of a MICA protein, a MICB protein, or both MICA and MICB protein. In some embodiments, the MICA protein is membrane-bound MICA protein, soluble MICA protein, or both. In some embodiments, the MICB protein is membrane-bound MICB protein, soluble MICB protein, or both. In some embodiments, the monoclonal antibody or antigen-binding fragment thereof is selected from a whole immunoglobulin, an scFv, a Fab, a $F(ab')_2$, or a disulfide linked Fv. In some embodiments, the monoclonal antibody or antigen-binding fragment thereof is an IgG or IgM. In some embodiments, the monoclonal antibody or fragment thereof is humanized or chimeric.

Disclosed herein, in certain embodiments, are monoclonal antibodies or an antigen-binding fragments thereof, comprising at least one of a heavy chain complementarity determining region 1 (CDR1) sequence at least 80% identical to SEQ ID NO: 4, a heavy chain complementarity determining region 2 (CDR2) sequence at least 80% identical to SEQ ID NO: 5, and a heavy chain complementarity determining region 3 (CDR3) sequence at least 80% identical to SEQ ID NO: 6. Disclosed herein, in certain embodiments, are monoclonal antibodies or an antigen-binding fragments thereof, comprising at least one of a heavy chain complementarity determining region 1 (CDR1) sequence at least 90% identical to SEQ ID NO: 4, a heavy chain complementarity determining region 2 (CDR2) sequence at least 90% identical to SEQ ID NO: 5, and a heavy chain complementarity determining region 3 (CDR3) sequence at least 90% identical to SEQ ID NO: 6. Disclosed herein, in certain embodiments, are monoclonal antibodies or an antigen-binding fragments thereof, comprising at least one of a heavy chain complementarity determining region 1 (CDR1) sequence at least 95% identical to SEQ ID NO: 4, a heavy chain complementarity determining region 2 (CDR2) sequence at least 95% identical to SEQ ID NO: 5, and a heavy chain complementarity determining region 3 (CDR3) sequence at least 95% identical to SEQ ID NO: 6. Disclosed herein, in certain embodiments, are monoclonal antibodies or an antigen-binding fragments thereof, comprising at least one of a heavy chain complementarity determining region 1 (CDR1) sequence at least 99% identical to SEQ ID NO: 4, a heavy chain complementarity determining region 2 (CDR2) sequence at least 99% identical to SEQ ID NO: 5, and a heavy chain complementarity determining region 3 (CDR3) sequence at least 99% identical to SEQ ID NO: 6. Disclosed herein, in certain embodiments, are monoclonal antibodies or an antigen-binding fragments thereof, comprising at least one of a heavy chain complementarity determining region 1 (CDR1) sequence 100% identical to SEQ ID NO: 4, a heavy chain complementarity determining region 2 (CDR2) sequence 100% identical to SEQ ID NO: 5, and a heavy chain complementarity determining region 3 (CDR3) sequence 100% identical to SEQ ID NO: 6. Disclosed herein, in certain embodiments, are monoclonal antibodies or an antigen-binding fragments thereof, comprising at least one of a heavy chain complementarity determining region 1 (CDR1) sequence at least 80% identical to SEQ ID NO: 4, a heavy chain complementarity determining region 2 (CDR2) sequence at least 80% identical to SEQ ID NO: 5, and a heavy chain complementarity determining region 3 (CDR3) sequence at least 80% identical to SEQ ID NO: 6, wherein the monoclonal antibody or antigen-binding fragment thereof comprises a heavy chain that does not have an amino acid sequence set forth as SEQ ID NO: 10, or wherein the monoclonal antibody or antigen-binding fragment thereof comprises a light chain that does not have an amino acid sequence set forth as SEQ ID NO: 9. Disclosed herein, in certain embodiments, are monoclonal antibodies or an antigen-binding fragments thereof, comprising at least one of a heavy chain complementarity determining region 1 (CDR1) sequence at least 90% identical to SEQ ID NO: 4, a heavy chain complementarity determining region 2 (CDR2) sequence at least 90% identical to SEQ ID NO: 5, and a heavy chain complementarity determining region 3 (CDR3) sequence at least 90% identical to SEQ ID NO: 6, wherein the monoclonal antibody or antigen-binding fragment thereof comprises a heavy chain that does not have an amino acid sequence set forth as SEQ ID NO: 10, or wherein the monoclonal antibody or antigen-binding fragment thereof comprises a light chain that does not have an amino acid sequence set forth as SEQ ID NO: 9. Disclosed herein, in certain embodiments, are monoclonal antibodies or an antigen-binding fragments thereof, comprising at least one of a heavy chain complementarity determining region 1 (CDR1) sequence at least 95% identical to SEQ ID NO: 4, a heavy chain complementarity determining region 2 (CDR2) sequence at least 95% identical to SEQ ID NO: 5, and a heavy chain complementarity determining region 3 (CDR3) sequence at least 95% identical to SEQ ID NO: 6, wherein the monoclonal antibody or antigen-binding fragment thereof comprises a heavy chain that does not have an amino acid sequence set forth as SEQ ID NO: 10, or wherein the monoclonal antibody or antigen-binding fragment thereof comprises a light chain that does not have an amino acid sequence set forth as SEQ ID NO: 9. Disclosed herein, in certain embodiments, are monoclonal antibodies or an antigen-binding fragments thereof, comprising at least one of a heavy chain complementarity determining region 1 (CDR1) sequence at least 99% identical to SEQ ID NO: 4, a heavy chain complementarity determining region 2 (CDR2) sequence at least 99% identical to SEQ ID NO: 5, and a heavy chain complementarity determining region 3 (CDR3) sequence at least 99% identical to SEQ ID NO: 6, wherein the monoclonal antibody or antigen-binding fragment thereof comprises a heavy chain that does not have an amino acid sequence set forth as SEQ ID NO: 10, or wherein the monoclonal antibody or antigen-binding fragment thereof comprises a light chain that does not have an amino acid sequence set forth as SEQ ID NO: 9. Disclosed herein, in certain embodiments, are monoclonal antibodies or an antigen-binding fragments thereof, comprising at least one of a heavy chain complementarity determining region 1 (CDR1) sequence 100% identical to SEQ ID NO: 4, a heavy chain complementarity determining region 2 (CDR2) sequence 100% identical to SEQ ID NO: 5, and a heavy chain complementarity determining region 3 (CDR3) sequence 100% identical to SEQ ID NO: 6, wherein the monoclonal antibody or antigen-binding fragment thereof comprises a heavy chain that does not have an amino acid sequence set forth as SEQ ID NO: 10, or wherein the monoclonal antibody or antigen-binding fragment thereof comprises a light chain that does not have an amino acid sequence set forth as SEQ ID NO: 9. In some embodiments, the monoclonal antibody or antigen-binding fragment thereof comprises at least one of a light chain complementarity determining region 1 (CDR1) sequence at least 80% identical to SEQ ID NO: 1, a light chain complementarity determining region 2 (CDR2) sequence at least 80% identical to SEQ ID NO: 2, and a light chain complementarity determining region 3 (CDR3) sequence at least 80% identical to SEQ ID NO: 3. In some embodiments, the monoclonal antibody or antigen-binding fragment thereof comprises at least one of a light chain complementarity determining region 1 (CDR1) sequence at least 90% identical to SEQ ID NO: 1, a light chain complementarity determining region 2 (CDR2) sequence at least 90% identical to SEQ ID NO: 2, and a light chain complementarity determining region 3 (CDR3) sequence at least 90% identical to SEQ ID NO: 3. In some embodiments, the monoclonal antibody or antigen-binding fragment thereof comprises at least one of a light chain complementarity determining region 1 (CDR1) sequence at least 95% identical to SEQ ID NO: 1, a light chain complementarity determining region 2 (CDR2) sequence at least 95% identical to SEQ ID NO: 2, and a light chain complementarity determining region 3 (CDR3) sequence at least 95% identical to SEQ ID NO: 3. In some embodiments, the monoclonal antibody or antigen-binding fragment thereof comprises at least one of a light chain complementarity determining region 1 (CDR1) sequence at least 99% identical to SEQ ID NO: 1, a light chain complementarity determining region 2 (CDR2) sequence at least 99% identical to SEQ ID NO: 2, and a light chain complementarity determining region 3 (CDR3) sequence at least 99% identical to SEQ ID NO: 3. In some embodiments, the monoclonal antibody or antigen-binding fragment thereof comprises at least one of a light chain complementarity determining region 1 (CDR1) sequence 100% identical to SEQ ID NO: 1, a light chain complementarity determining region 2 (CDR2) sequence 100% identical to SEQ ID NO: 2, and a light chain complementarity determining region 3 (CDR3) sequence 100% identical to SEQ ID NO: 3. In some embodiments, the monoclonal antibody or antigen-binding fragment thereof comprises a heavy chain variable domain (VH) comprising an amino acid sequence at least 80% identical to an amino acid sequence set forth as SEQ ID NO: 8. In some embodiments, the monoclonal antibody or antigen-binding fragment thereof comprises a light chain variable domain (VL) comprising an amino acid sequence at least 80% identical to an amino acid sequence set forth as SEQ ID NO: 7. In some embodiments, the monoclonal antibody or antigen-binding fragment thereof comprises a light chain variable domain (VL) comprising an amino acid sequence at least 80% identical to an amino acid sequence set forth as SEQ ID NO: 7. In some embodiments, the monoclonal antibody or antigen-binding fragment thereof comprises a heavy chain variable domain (VH) comprising an amino acid sequence at least 80% identical to an amino acid sequence set forth as SEQ ID NO: 8. In some embodiments, the heavy chain comprises an amino acid sequence wherein at least 1 to 10 amino acids of amino acid sequence set forth as SEQ ID NO: 10 are modified. In some embodiments, the light chain comprises an amino acid sequence wherein at least 1 to 10 amino acids of amino acid sequence set forth as SEQ ID NO: 9 are modified. In some embodiments, the monoclonal antibody or antigen-binding fragment thereof specifically binds to a MICA protein, a MICB protein, or both MICA and MICB protein. In some embodiments, the monoclonal antibody or antigen-binding fragment thereof binds to an alpha-3 domain of a MICA protein, a MICB protein, or both MICA and MICB protein. In some embodiments, the MICA protein is membrane-bound MICA protein, soluble MICA protein, or both. In some embodiments, the MICB protein is membrane-bound MICB protein, soluble MICB protein, or both. In some embodiments, the monoclonal antibody or antigen-binding fragment thereof is selected from a whole immunoglobulin, an scFv, a Fab, a $F(ab')_2$, or a disulfide linked Fv. In some embodiments, the monoclonal antibody or antigen-binding fragment thereof is an IgG or IgM. In some embodiments, the monoclonal antibody or fragment thereof is humanized or chimeric.

Disclosed herein, in certain embodiments, are pharmaceutical compositions comprising: a monoclonal antibody or an antigen-binding fragment thereof according to any of the disclosures herein; and a pharmaceutically acceptable carrier or excipient.

Disclosed herein, in certain embodiments, are methods of treating cancer in an individual in need thereof, comprising administering to the individual an effective amount of a monoclonal antibody or an antigen-binding fragment thereof comprising at least one of a light chain complementarity determining region 1 (CDR1) sequence at least 80% identical to SEQ ID NO: 1, a light chain complementarity determining region 2 (CDR2) sequence at least 80% identical to SEQ ID NO: 2, and a light chain complementarity determining region 3 (CDR3) sequence at least 80% identical to SEQ ID NO: 3. In some embodiments, the monoclonal antibody or antigen-binding fragment thereof comprises at least one of a heavy chain complementarity determining region 1 (CDR1) sequence at least 80% identical to SEQ ID NO: 4, a heavy chain complementarity determining region 2 (CDR2) sequence at least 80% identical to SEQ ID NO: 5, and a heavy chain complementarity determining region 3 (CDR3) sequence at least 80% identical to SEQ ID NO: 6. In some embodiments, the monoclonal antibody or antigen-binding fragment thereof comprises a light chain variable domain (VL) comprising an amino acid sequence at least 80% identical to an amino acid sequence set forth as SEQ ID NO: 7. In some embodiments, the monoclonal antibody or antigen-binding fragment thereof comprises a heavy chain variable domain (VH) comprising an amino acid sequence at least 80% identical to an amino acid sequence set forth as SEQ ID NO: 8. In some embodiments, the monoclonal antibody or antigen-binding fragment thereof comprises a heavy chain variable domain (VH) comprising an amino acid sequence at least 80% identical to an amino acid sequence set forth as SEQ ID NO: 8. In some embodiments, the monoclonal antibody or antigen-binding fragment thereof comprises a light chain variable domain (VL) comprising an amino acid sequence at least 80% identical to an amino acid sequence set forth as SEQ ID NO: 7. In some embodiments, the monoclonal antibody or antigen-binding fragment thereof specifically binds to a MICA protein, a MICB protein, or both MICA and MICB protein. In some embodiments, the monoclonal antibody or antigen-binding fragment thereof binds to an alpha-3 domain of a MICA protein, a MICB protein, or both MICA and MICB protein. In some embodiments, the MICA protein is membrane-bound MICA protein, soluble MICA protein, or both. In some embodiments, the MICB protein is membrane-bound MICB protein, soluble MICB protein, or both. In some embodiments, the monoclonal antibody or antigen-binding fragment thereof is selected from a whole immunoglobulin, an scFv, a Fab, a $F(ab')_2$, or a disulfide linked Fv. In some embodiments, the monoclonal antibody or antigen-binding fragment thereof is an IgG or IgM. In some embodiments, the monoclonal antibody or fragment thereof is humanized or chimeric. In some embodiments, the monoclonal antibody or antigen binding fragment thereof reduces level of soluble MICA protein, soluble MICB protein, or both. In some embodiments, the monoclonal antibody or antigen binding fragment thereof reduces shedding of soluble MICA protein, soluble MICB protein, or both. In some embodiments, the monoclonal antibody or antigen binding fragment thereof inhibits shedding of soluble MICA protein, soluble MICB protein, or both. In some embodiments, the cancer is hepatocellular carcinoma.

Disclosed herein, in certain embodiments, are methods of treating cancer in an individual in need thereof, comprising administering to the individual an effective amount of a monoclonal antibody or an antigen-binding fragment thereof comprising at least one of a heavy chain complementarity determining region 1 (CDR1) sequence at least 80% identical to SEQ ID NO: 4, a heavy chain complementarity determining region 2 (CDR2) sequence at least 80% identical to SEQ ID NO: 5, and a heavy chain complementarity determining region 3 (CDR3) sequence at least 80% identical to SEQ ID NO: 6. In some embodiments, the monoclonal antibody or antigen-binding fragment thereof comprises at least one of a light chain complementarity determining region 1 (CDR1) sequence at least 80% identical to SEQ ID NO: 1, a light chain complementarity determining region 2 (CDR2) sequence at least 80% identical to SEQ ID NO: 2, and a light chain complementarity determining region 3 (CDR3) sequence at least 80% identical to SEQ ID NO: 3. In some embodiments, the monoclonal antibody or antigen-binding fragment thereof comprises a heavy chain variable domain (VH) comprising an amino acid sequence at least 80% identical to an amino acid sequence set forth as SEQ ID NO: 8. In some embodiments, the monoclonal antibody or antigen-binding fragment thereof comprises a light chain variable domain (VL) comprising an amino acid sequence at least 80% identical to an amino acid sequence set forth as SEQ ID NO: 7. In some embodiments, the monoclonal antibody or antigen-binding fragment thereof comprises a light chain variable domain (VL) comprising an amino acid sequence at least 80% identical to an amino acid sequence set forth as SEQ ID NO: 7. In some embodiments, the monoclonal antibody or antigen-binding fragment thereof comprises a heavy chain variable domain (VH) comprising an amino acid sequence at least 80% identical to an amino acid sequence set forth as SEQ ID NO: 8. In some embodiments, the monoclonal antibody or antigen-binding fragment thereof specifically binds to a MICA protein, a MICB protein, or both MICA and MICB protein. In some embodiments, the monoclonal antibody or antigen-binding fragment thereof binds to an alpha-3 domain of a MICA protein, a MICB protein, or both MICA and MICB protein. In some embodiments, the MICA protein is membrane-bound MICA protein, soluble MICA protein, or both. In some embodiments, the MICB protein is membrane-bound MICB protein, soluble MICB protein, or both. In some embodiments, the monoclonal antibody or antigen-binding fragment thereof is selected from a whole immunoglobulin, an scFv, a Fab, a $F(ab')_2$, or a disulfide linked Fv. In some embodiments, the monoclonal antibody or antigen-binding fragment thereof is an IgG or IgM. In some embodiments, the monoclonal antibody or fragment thereof is humanized or chimeric. In some embodiments, the monoclonal antibody or antigen binding fragment thereof reduces level of soluble MICA protein, soluble MICB protein, or both. In some embodiments, the monoclonal antibody or antigen binding fragment thereof reduces shedding of soluble MICA protein, soluble MICB protein, or both. In some embodiments, the monoclonal antibody or antigen binding fragment thereof inhibits shedding of soluble MICA protein, soluble MICB protein, or both. In some embodiments, the cancer is hepatocellular carcinoma.

Disclosed herein, in certain embodiments, are methods of treating hepatocellular carcinoma in an individual in need thereof, comprising administering to the individual an effective amount of a monoclonal antibody or an antigen-binding fragment thereof comprising at least one of a light chain complementarity determining region 1 (CDR1) sequence at least 80% identical to SEQ ID NO: 1, a light chain complementarity determining region 2 (CDR2) sequence at least 80% identical to SEQ ID NO: 2, and a light chain complementarity determining region 3 (CDR3) sequence at least 80% identical to SEQ ID NO: 3. In some embodiments, the monoclonal antibody or antigen-binding fragment thereof comprises at least one of a heavy chain complementarity determining region 1 (CDR1) sequence at least 80% identical to SEQ ID NO: 4, a heavy chain complementarity determining region 2 (CDR2) sequence at least 80% identical to SEQ ID NO: 5, and a heavy chain complementarity determining region 3 (CDR3) sequence at least 80% identical to SEQ ID NO: 6. In some embodiments, the monoclonal antibody or antigen-binding fragment thereof comprises a light chain variable domain (VL) comprising an amino acid sequence at least 80% identical to an amino acid sequence set forth as SEQ ID NO: 7. In some embodiments, the monoclonal antibody or antigen-binding fragment thereof comprises a heavy chain variable domain (VH) comprising an amino acid sequence at least 80% identical to an amino acid sequence set forth as SEQ ID NO: 8. In some embodiments, the monoclonal antibody or antigen-binding fragment thereof comprises a heavy chain variable domain (VH) comprising an amino acid sequence at least 80% identical to an amino acid sequence set forth as SEQ ID NO: 8. In some embodiments, the monoclonal antibody or antigen-binding fragment thereof comprises a light chain variable domain (VL) comprising an amino acid sequence at least 80% identical to an amino acid sequence set forth as SEQ ID NO: 7. In some embodiments, the monoclonal antibody or antigen-binding fragment thereof specifically binds to a MICA protein, a MICB protein, or both MICA and MICB protein. In some embodiments, the monoclonal antibody or antigen-binding fragment thereof binds to an alpha-3 domain of a MICA protein, a MICB protein, or both MICA and MICB protein. In some embodiments, the MICA protein is membrane-bound MICA protein, soluble MICA protein, or both. In some embodiments, the MICB protein is membrane-bound MICB protein, soluble MICB protein, or both. In some embodiments, the monoclonal antibody or antigen-binding fragment thereof is selected from a whole immunoglobulin, an scFv, a Fab, a $F(ab')_2$, or a disulfide linked Fv. In some embodiments, the monoclonal antibody or antigen-binding fragment thereof is an IgG or IgM. In some embodiments, the monoclonal antibody or fragment thereof is humanized or chimeric. In some embodiments, the monoclonal antibody or antigen binding fragment thereof reduces level of soluble MICA protein, soluble MICB protein, or both. In some embodiments, the monoclonal antibody or antigen binding fragment thereof reduces shedding of soluble MICA protein, soluble MICB protein, or both. In some embodiments, the monoclonal antibody or antigen binding fragment thereof inhibits shedding of soluble MICA protein, soluble MICB protein, or both.

Disclosed herein, in certain embodiments, are methods of treating hepatocellular carcinoma in an individual in need thereof, comprising administering to the individual an effective amount of a monoclonal antibody or an antigen-binding fragment thereof comprising at least one of a heavy chain complementarity determining region 1 (CDR1) sequence at least 80% identical to SEQ ID NO: 4, a heavy chain complementarity determining region 2 (CDR2) sequence at least 80% identical to SEQ ID NO: 5, and a heavy chain complementarity determining region 3 (CDR3) sequence at least 80% identical to SEQ ID NO: 6. In some embodiments, the monoclonal antibody or antigen-binding fragment thereof comprises at least one of a light chain complementarity determining region 1 (CDR1) sequence at least 80% identical to SEQ ID NO: 1, a light chain complementarity determining region 2 (CDR2) sequence at least 80% identical to SEQ ID NO: 2, and a light chain complementarity determining region 3 (CDR3) sequence at least 80% identical to SEQ ID NO: 3. In some embodiments, the monoclonal antibody or antigen-binding fragment thereof comprises a heavy chain variable domain (VH) comprising an amino acid sequence at least 80% identical to an amino acid sequence set forth as SEQ ID NO: 8. In some embodiments, the monoclonal antibody or antigen-binding fragment thereof comprises a light chain variable domain (VL) comprising an amino acid sequence at least 80% identical to an amino acid sequence set forth as SEQ ID NO: 7. In some embodiments, the monoclonal antibody or antigen-binding fragment thereof comprises a light chain variable domain (VL) comprising an amino acid sequence at least 80% identical to an amino acid sequence set forth as SEQ ID NO: 7. In some embodiments, the monoclonal antibody or antigen-binding fragment thereof comprises a heavy chain variable domain (VH) comprising an amino acid sequence at least 80% identical to an amino acid sequence set forth as SEQ ID NO: 8. In some embodiments, the monoclonal antibody or antigen-binding fragment thereof specifically binds to a MICA protein, a MICB protein, or both MICA and MICB protein. In some embodiments, the monoclonal antibody or antigen-binding fragment thereof binds to an alpha-3 domain of a MICA protein, a MICB protein, or both MICA and MICB protein. In some embodiments, the MICA protein is membrane-bound MICA protein, soluble MICA protein, or both. In some embodiments, the MICB protein is membrane-bound MICB protein, soluble MICB protein, or both. In some embodiments, the monoclonal antibody or antigen-binding fragment thereof is selected from a whole immunoglobulin, an scFv, a Fab, a $F(ab')_2$, or a disulfide linked Fv. In some embodiments, the monoclonal antibody or antigen-binding fragment thereof is an IgG or IgM. In some embodiments, the monoclonal antibody or fragment thereof is humanized or chimeric. In some embodiments, the monoclonal antibody or antigen binding fragment thereof reduces level of soluble MICA protein, soluble MICB protein, or both. In some embodiments, the monoclonal antibody or antigen binding fragment thereof reduces shedding of soluble MICA protein, soluble MICB protein, or both. In some embodiments, the monoclonal antibody or antigen binding fragment thereof inhibits shedding of soluble MICA protein, soluble MICB protein, or both.

Disclosed herein, in certain embodiments, are methods of reducing level of soluble MICA protein, soluble MICB protein, or both in an individual in need thereof, comprising administering to the individual an effective amount of a monoclonal antibody or an antigen-binding fragment thereof comprising at least one of a light chain complementarity determining region 1 (CDR1) sequence at least 80% identical to SEQ ID NO: 1, a light chain complementarity determining region 2 (CDR2) sequence at least 80% identical to SEQ ID NO: 2, and a light chain complementarity determining region 3 (CDR3) sequence at least 80% identical to SEQ ID NO: 3. In some embodiments, the monoclonal antibody or antigen-binding fragment thereof comprises at least one of a heavy chain complementarity determining region 1 (CDR1) sequence at least 80% identical to SEQ ID NO: 4, a heavy chain complementarity determining region 2 (CDR2) sequence at least 80% identical to SEQ ID NO: 5, and a heavy chain complementarity determining region 3 (CDR3) sequence at least 80% identical to SEQ ID NO: 6. In some embodiments, the monoclonal antibody or antigen-binding fragment thereof comprises a light chain variable domain (VL) comprising an amino acid sequence at least 80% identical to an amino acid sequence set forth as SEQ ID NO: 7. In some embodiments, the monoclonal antibody or antigen-binding fragment thereof comprises a heavy chain variable domain (VH) comprising an amino acid sequence at least 80% identical to an amino acid sequence set forth as SEQ ID NO: 8. In some embodiments, the monoclonal antibody or antigen-binding fragment thereof comprises a heavy chain variable domain (VH) comprising an amino acid sequence at least 80% identical to an amino acid sequence set forth as SEQ ID NO: 8. In some embodiments, the monoclonal antibody or antigen-binding fragment thereof comprises a light chain variable domain (VL) comprising an amino acid sequence at least 80% identical to an amino acid sequence set forth as SEQ ID NO: 7. In some embodiments, the monoclonal antibody or antigen-binding fragment thereof specifically binds to a MICA protein, a MICB protein, or both MICA and MICB protein. In some embodiments, the monoclonal antibody or antigen-binding fragment thereof binds to an alpha-3 domain of a MICA protein, a MICB protein, or both MICA and MICB protein. In some embodiments, the MICA protein is soluble MICA protein. In some embodiments, the MICB protein is soluble MICB protein. In some embodiments, the monoclonal antibody or antigen-binding fragment thereof is selected from a whole immunoglobulin, an scFv, a Fab, a $F(ab')_2$, or a disulfide linked Fv. In some embodiments, the monoclonal antibody or antigen-binding fragment thereof is an IgG or IgM. In some embodiments, the monoclonal antibody or fragment thereof is humanized or chimeric. In some embodiments, the monoclonal antibody or antigen-binding fragment thereof reduces or inhibits shedding of soluble MICA protein, soluble MICB protein, or both, thereby reducing level of soluble MICA protein, soluble MICB protein, or both in the individual. In some embodiments, the individual has a cancer characterized by elevated levels of soluble MICA protein, soluble MICB protein, or both. In some embodiments, the cancer is hepatocellular carcinoma.

Disclosed herein, in certain embodiments, are methods of reducing level of soluble MICA protein, soluble MICB protein, or both in an individual in need thereof, comprising administering to the individual an effective amount of a monoclonal antibody or an antigen-binding fragment thereof comprising at least one of a heavy chain complementarity determining region 1 (CDR1) sequence at least 80% identical to SEQ ID NO: 4, a heavy chain complementarity determining region 2 (CDR2) sequence at least 80% identical to SEQ ID NO: 5, and a heavy chain complementarity determining region 3 (CDR3) sequence at least 80% identical to SEQ ID NO: 6. In some embodiments, the monoclonal antibody or antigen-binding fragment thereof comprises at least one of a light chain complementarity determining region 1 (CDR1) sequence at least 80% identical to SEQ ID NO: 1, a light chain complementarity determining region 2 (CDR2) sequence at least 80% identical to SEQ ID NO: 2, and a light chain complementarity determining region 3 (CDR3) sequence at least 80% identical to SEQ ID NO: 3. In some embodiments, the monoclonal antibody or antigen-binding fragment thereof comprises a heavy chain variable domain (VH) comprising an amino acid sequence at least 80% identical to an amino acid sequence set forth as SEQ ID NO: 8. In some embodiments, the monoclonal antibody or antigen-binding fragment thereof comprises a light chain variable domain (VL) comprising an amino acid sequence at least 80% identical to an amino acid sequence set forth as SEQ ID NO: 7. In some embodiments, the monoclonal antibody or antigen-binding fragment thereof comprises a light chain variable domain (VL) comprising an amino acid sequence at least 80% identical to an amino acid sequence set forth as SEQ ID NO: 7. In some embodiments, the monoclonal antibody or antigen-binding fragment thereof comprises a heavy chain variable domain (VH) comprising an amino acid sequence at least 80% identical to an amino acid sequence set forth as SEQ ID NO: 8. In some embodiments, the monoclonal antibody or antigen-binding fragment thereof specifically binds to a MICA protein, a MICB protein, or both MICA and MICB protein. In some embodiments, the monoclonal antibody or antigen-binding fragment thereof binds to an alpha-3 domain of a MICA protein, a MICB protein, or both MICA and MICB protein. In some embodiments, the MICA protein is soluble MICA protein. In some embodiments, the MICB protein is soluble MICB protein. In some embodiments, the monoclonal antibody or antigen-binding fragment thereof is selected from a whole immunoglobulin, an scFv, a Fab, a $F(ab')_2$, or a disulfide linked Fv. In some embodiments, the monoclonal antibody or antigen-binding fragment thereof is an IgG or IgM. In some embodiments, the monoclonal antibody or fragment thereof is humanized or chimeric. In some embodiments, the monoclonal antibody or antigen-binding fragment thereof reduces or inhibits shedding of soluble MICA protein, soluble MICB protein, or both, thereby reducing level of soluble MICA protein, soluble MICB protein, or both in the individual. In some embodiments, the individual has a cancer characterized by elevated levels of soluble MICA protein, soluble MICB protein, or both. In some embodiments, the cancer is hepatocellular carcinoma.

Disclosed herein, in certain embodiments, are monoclonal antibodies or an antigen-binding fragments thereof according to any of the disclosures herein for use in treating cancer in an individual in need thereof. Also disclosed herein, in certain embodiments, are monoclonal antibodies or an antigen-binding fragments thereof according to any of the disclosures herein for use in preparation of a medicament for treating cancer in an individual in need thereof. In some embodiments, the cancer is hepatocellular carcinoma.

BRIEF DESCRIPTION OF THE DRAWINGS

An understanding of the features and advantages of the present invention will be obtained by reference to the following detailed description that sets forth illustrative embodiments, in which the principles of the invention are utilized, and the accompanying drawings of which.

DETAILED DESCRIPTION

Figure 1:
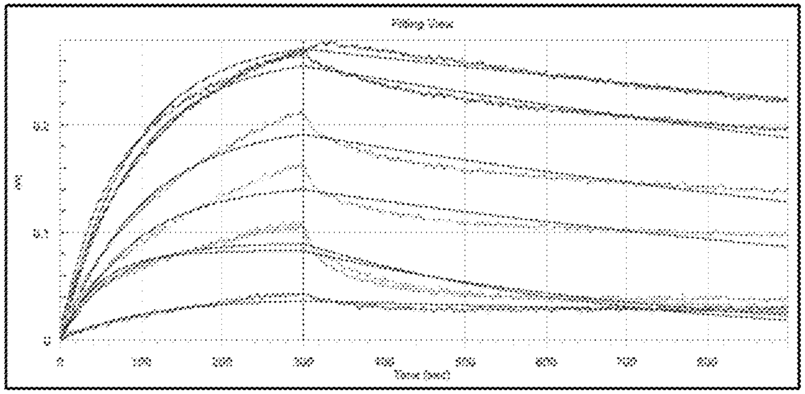
FIG. 1 illustrates kinetic measurements of antibody PDI-1 to MICA antigens (MICA*01 and MICA*08) by BioLayer Interferometry.
Figure 1:
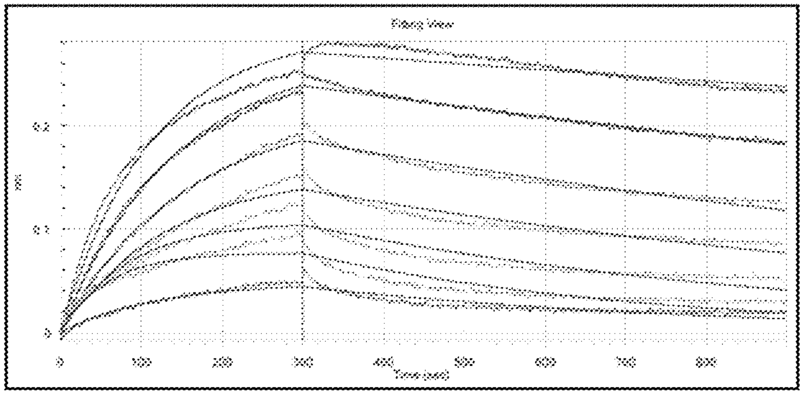

Disclosed herein, in some embodiments, are monoclonal antibodies that bind specifically to MICA/B. In some embodiments, MICA/B antibodies herein bind to MICA/B proteins or fragments thereof and modulate immune response in an individual, thereby treating cancer (e.g. hepatocellular carcinoma).

Major histocompatibility complex class I-related chain A and B (MICA/B) are two stress-inducible ligands for natural killer cell (NK) receptor NKG2D and play an important role in mediating the cytotoxicity of NK and T cells. Soluble MICA/B shed by diseased cells (e.g. cancer cells) desensitizes NK and T cells through binding of NKG2D receptor, thereby suppressing the immune response. Accordingly, modulation of MICA/B is useful in modulating an immune response in an individual, for example, in an individual suffering from cancer. Antibodies binding to MICA/B and modulating its activity are desirable for the development of novel therapeutics for treatment of cancer.

Certain Terminology

As used herein "MICA/B" refers to MICA protein, MICB protein or both MICA and MICB proteins, including their variants, isoforms, and species homologs of human MICA/B.

As used herein "antibody" refers to a glycoprotein which exhibits binding specificity to a specific antigen. An antibody often comprises a variable domain and a constant domain in each of a heavy chain and a light chain. Accordingly, most antibodies have a heavy chain variable domain (VH) and a light chain variable domain (VL) that together form the portion of the antibody that binds to the antigen. Within each variable domain are three complementarity determining regions (CDR) which form loops in the heavy chain variable domain (VH) and light chain variable domain (VL) that contact the surface of the antigen. Antibodies herein also include "antigen binding portion" or fragments of the antibody that are capable of binding to the antigen.

As used herein "chimeric" antibodies are antibodies having a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see e.g., Morrison et al., Proc. Natl. Acad. Sci. USA 81:6851-6855 (1984)). "Humanized antibodies" herein refers chimeric antibodies having human sequences substituted in the antibody sequence.

The terms "recipient", "individual", "subject", "host", and "patient", are used interchangeably herein and in some cases, refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc. In some embodiments, the mammal is human.

As used herein, the terms "treatment," "treating," and the like, in some cases, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a disease or disorder (e.g. cancer) in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. Treating may refer to any indicia of success in the treatment or amelioration or prevention of a cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms is based on one or more objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with diseases (e.g. cancer). The term "therapeutic effect" refers to the reduction, elimination, or prevention of the disease, symptoms of the disease, or side effects of the disease in the subject.

A "therapeutically effective amount" in some cases means the amount that, when administered to a subject for treating a disease, is sufficient to effect treatment for that disease.

As used herein, singular forms "a", "and," and "the" include plural referents unless the context clearly indicates otherwise. Thus, for example, reference to "an antibody" includes a plurality of antibodies and reference to "an antibody" in some embodiments includes multiple antibodies, and so forth.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. In another example, reference to a range of 1-5,000 fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and so forth.

"About" a number, as used herein, refers to range including the number and ranging from 10% below that number to 10% above that number. "About" a range refers to 10% below the lower limit of the range, spanning to 10% above the upper limit of the range.

MICA/B

Disclosed herein, in some embodiments, are monoclonal antibodies that bind specifically to MICA/B.

Major Histocompatibility Complex (MHC) class I Chain-related gene A and gene B protein (MICA/B) are glycosylated, polymorphic and membrane-anchored non-classical MHC class I proteins. MICA/B are related to MHC class I and have similar domain structure comprising three extracellular Ig-like domains (alpha-1, alpha-2 and alpha-3), a transmembrane domain and a C-terminal cytoplasmic tail. However, MICA/B do not associate with β2-microglobulin, lack a CD8 binding site and do not present any antigens. MICA/B are ligands to C-type lectin-like activating receptor Natural Killer Group 2D (NKG2D) on immune effector cells, including NK, NKT and both αβ and γδ $CD8^+$ T cells. The interaction of MICA/B and NKG2D plays a role in tumor surveillance, and immune response.

MICA/B proteins are expressed normally at low levels in normal cells, but are induced to higher levels in stressed or transformed cells (e.g. cancer cells). The interaction of NKG2D-bearing immune effector cells with stressed or diseased cells expressing MICA/B ligands on the cell surface creates a cellular immune response against the stressed/diseased cell that culminates in the death of the MICA/B expressing cells. In cancer cells, the truncated MICA/B proteins (proteins that lack the transmembrane domain and cytoplasmic tail but retain the three extracellular domain comprising alpha-1, -2 and -3 domains) are frequently shed into the blood by the action of proteases and results in the down-modulation (receptor internalization) of its intended receptor, NKG2D, on effector immune cells. In some embodiments, MICA/B glycoproteins are produced intracellularly that are not routinely destined to become cell surface membrane-bound, but instead are incorporated within exosomes and released outside the cell where interaction with NKG2D receptors on immune cells occurs. These truncated or soluble MICA/B ligands shed from the surface of cancer cells function like decoy molecules and lead to down-modulation of the NKG2D receptor on immune effector cells such as NK, NKT and various $CD8^+$ T cells. In some embodiments, the formation of soluble MICA/B leads to the unusual situation where the effectors of the innate defense system, whose natural role is to seek and destroy transformed cells, are shut down by the immunosuppressive actions of these decoy ligand molecules, thereby enabling the cancer cells to hide from the immune system and to grow unchecked.

Hepatocellular Carcinoma (HCC)

In some embodiments, MICA/B antibodies disclosed herein bind to MICA/B proteins or fragments thereof and ies comprise at least one heavy chain comprising a heavy chain variable domain (VH) and at least one light chain comprising a light chain variable domain (VL). Each VH and VL comprises three complementarity determining regions (CDR). The amino acid sequences of the VH and VL and the CDRs determine the antigen binding specificity and antigen binding strength of the antibody. The amino acid sequences of the VH and VL and the CDRs are summarized in Table 1.

TABLE 1

Anti-MICA/B Monoclonal Antibody (PDI-1) Sequences

| | SEQUENCE | SEQ ID NO: |
|---|---|---|
| Light Chain CDR1 | SASQGISNYLN | 1 |
| Light Chain CDR2 | TSLLHSG | 2 |
| Light Chain CDR3 | QQYSKFPRT | 3 |
| Heavy Chain CDR1 | GYTFTNYGMN | 4 |
| Heavy Chain CDR2 | INTYTGEPTYADDFKG | 5 |
| Heavy Chain CDR3 | NYGNYLFDY | 6 |
| Light Chain Variable domain | DIQMTQTTSSLSASLGDRVTISCSASQGISNYLNWYQQKPDGTL<br>KLLIQYTSLLHSGVPSRFSGSGSGTEYSLTISNLEPEDIATYFCQQ<br>YSKFPRTFGGGTKLEIKR | 7 |
| Heavy Chain Variable domain | QIQLVQSGPELKKSGETVKISCKAFGYTFTNYGMNWVKQAPGK<br>GLKWMGWINTYTGEPTYADDFKGRFAFSLETSASTAYLQINHL<br>KNEDTATYFCARNYGNYLFDYWGQGTTLTVSS | 8 |
| Light Chain | METDTLLLWVLLLWVPGSTGDIQMTQTTSSLSASLGDRVTISCS<br>ASQGISNYLNWYQQKPDGTLKLLIQYTSLLHSGVPSRFSGSGSGT<br>EYSLTISNLEPEDIATYFCQQYSKFPRTFGGGTKLEIKRADAAPTV<br>SIFPPSSEQLTSGGASVVCFLNNFYPKDINVKWKIDGSERQNGVL<br>NSWTDQDSKDSTYSMSSTLTLTKDEYERHNSYTCEATHKTSTSP<br>IVKSFNRNEC** | 9 |
| Heavy Chain | METDTLLLWVLLLWVPGSTGQIQLVQSGPELKKSGETVKISCKA<br>FGYTFTNYGMNWVKQAPGKGLKWMGWINTYTGEPTYADDFK<br>GRFAFSLETSASTAYLQINHLKNEDTATYFCARNYGNYLFDYW<br>GQGTTLTVSSAKTTAPSVYPLAPVCGDTTGSSVTLGCLVKGYFP<br>EPVTLTWNSGSLSSGVHTFPAVLQSDLYTLSSSVTVTSSTWPSQS<br>ITCNVAHPASSTKVDKKIEPRGPTIKPCPPCKCPAPNLLGGPSVFI<br>FPPKIKDVLMISLSPIVTCVVVDVSEDDPDVQISWFVNNVEVHTA<br>QTQTHREDYNSTLRVVSALPIQHQDWMSGKEFKCKVNNKDLPA<br>PIERTISKPKGSVRAPQVYVLPPPEEEMTKKQVTLTCMVTDFMPE<br>DIYVEWTNNGKTELNYKNTEPVLDSDGSYFMYSKLRVEKKNW<br>VERNSYSCSVVHEGLHNHHTTKSFSRTPG ** | 10 |

modulate immune response in an individual, thereby treating cancer (e.g. hepatocellular carcinoma).

Hepatocellular carcinoma (HCC) is a primary malignancy of the liver and occurs predominantly in individuals with underlying chronic liver disease and cirrhosis. Tumors progress with local expansion, intrahepatic spread, and distant metastases. Hepatitis B and Hepatitis C predisposes individuals to the development of chronic liver disease and subsequent development of HCC. Obesity, diabetes, and alcohol abuse are some other causes that predispose individuals to the subsequent development of HCC.

MICA/B Antibodies

Provided herein are antibodies that specifically bind to MICA/B proteins. In some embodiments, MICA/B antibod- In some embodiments, the antibodies specifically bind to a MICA protein. In some embodiments, the antibodies specifically bind to a MICB protein. In some embodiments, the antibodies specifically bind to both MICA and MICB protein. In some embodiments, the antibodies bind to an alpha-3 domain of a MICA protein. In some embodiments, the antibodies bind to an alpha-3 domain of a MICB protein. In some embodiments, the antibodies bind to an alpha-3 domain of both MICA and MICB protein. In some embodiments, the antibodies bind to a MICA protein that is membrane-bound MICA protein. In some embodiments, the antibodies bind to a MICA protein that is soluble MICA protein. In some embodiments, the antibodies bind to a MICA protein that is both membrane-bound MICA protein and soluble MICA protein. In some embodiments, the antibodies bind to a MICB protein that is membrane-bound MICB protein. In some embodiments, the antibodies bind to a MICB protein that is soluble MICB protein. In some embodiments, the antibodies bind to a MICB protein that is both membrane-bound MICB protein and soluble MICB protein.

In some embodiments, antibodies that specifically bind to MICA/B are monoclonal antibodies. In some embodiments, the antibody is an antigen binding fragment. In some embodiments, the antibody is selected from a whole immunoglobulin, an scFv, a Fab, a F(ab')2, or a disulfide linked Fv. In some embodiments, the antibody is an IgG or an IgM. In some embodiments, the antibody is humanized. In some embodiments, the antibody is chimeric.

MICA/B Antibody Variable Domain

Disclosed herein are antibodies that specifically bind to MICA/B having a light chain comprising a light chain variable domain (VL). In some embodiments, antibodies binding to MICA/B comprise a light chain variable domain (VL) having an amino acid sequence at least about 70% identical to an amino acid sequence set forth as SEQ ID NO: 7. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7. In some embodiments, the VL has an amino acid sequence 100% identical to an amino acid sequence set forth as SEQ ID NO: 7.

Further disclosed herein are antibodies that specifically bind to MICA/B having a heavy chain comprising a heavy chain variable domain (VH). In some embodiments, antibodies binding to MICA/B comprise a heavy chain variable domain (VH) having an amino acid sequence at least about 70% identical to an amino acid sequence set forth as SEQ ID NO: 8. In some embodiments the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8. In some embodiments, the VH has an amino acid sequence 100% identical to an amino acid sequence set forth as SEQ ID NO: 8.

Also disclosed herein are antibodies binding to MICA/B comprising a light chain variable domain (VL) and a heavy chain variable domain (VH). In some embodiments, antibodies binding to MICA/B comprise a light chain variable domain (VL) having an amino acid sequence at least about 70% identical to an amino acid sequence set forth as SEQ ID NO: 7 and a heavy chain variable domain (VH) having an amino acid sequence at least about 70% identical to an amino acid sequence set forth as SEQ ID NO: 8. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8. In some embodiments, the VL has an amino acid sequence 100% identical to an amino acid sequence set forth as SEQ ID NO: 7 and the VH has an amino acid sequence 100% identical to an amino acid sequence set forth as SEQ ID NO: 8. In some embodiments, the monoclonal antibody or antigen-binding fragment thereof comprises a light chain that does not have an amino acid sequence set forth as SEQ ID NO: 9. In some embodiments, the light chain comprises an amino acid sequence wherein at least 1 to 10 amino acids of amino acid sequence set forth as SEQ ID NO: 9 are modified. In some embodiments, the light chain comprises an amino acid sequence wherein at least 1 amino acid of amino acid sequence set forth as SEQ ID NO: 9 is modified. In some embodiments, the light chain comprises an amino acid sequence wherein at least 2 amino acids of amino acid sequence set forth as SEQ ID NO: 9 are modified. In some embodiments, the light chain comprises an amino acid sequence wherein at least 3 amino acids of amino acid sequence set forth as SEQ ID NO: 9 are modified. In some embodiments, the light chain comprises an amino acid sequence wherein at least 4 amino acids of amino acid sequence set forth as SEQ ID NO: 9 are modified. In some embodiments, the light chain comprises an amino acid sequence wherein at least 5 amino acids of amino acid sequence set forth as SEQ ID NO: 9 are modified. In some embodiments, the light chain comprises an amino acid sequence wherein at least 6 amino acids of amino acid sequence set forth as SEQ ID NO: 9 are modified. In some embodiments, the light chain comprises an amino acid sequence wherein at least 7 amino acids of amino acid sequence set forth as SEQ ID NO: 9 are modified. In some embodiments, the light chain comprises an amino acid sequence wherein at least 8 amino acids of amino acid sequence set forth as SEQ ID NO: 9 are modified. In some embodiments, the light chain comprises an amino acid sequence wherein at least 9 amino acids of amino acid sequence set forth as SEQ ID NO: 9 are modified. In some embodiments, the light chain comprises an amino acid sequence wherein at least 10 amino acids of amino acid sequence set forth as SEQ ID NO: 9 are modified. In some embodiments, the monoclonal antibody or antigen-binding fragment thereof comprises a heavy chain that does not have an amino acid sequence set forth as SEQ ID NO: 10. In some embodiments, the heavy chain comprises an amino acid sequence wherein at least 1 to 10 amino acids of amino acid sequence set forth as SEQ ID NO: 10 are modified. In some embodiments, the heavy chain comprises an amino acid sequence wherein at least 1 amino acid of amino acid sequence set forth as SEQ ID NO: 10 is modified. In some embodiments, the heavy chain comprises an amino acid sequence wherein at least 2 amino acids of amino acid sequence set forth as SEQ ID NO: 10 are modified. In some embodiments, the heavy chain comprises an amino acid sequence wherein at least 3 amino acids of amino acid sequence set forth as SEQ ID NO: 10 are modified. In some embodiments, the heavy chain comprises an amino acid sequence wherein at least 4 amino acids of amino acid sequence set forth as SEQ ID NO: 10 are modified. In some embodiments, the heavy chain comprises an amino acid sequence wherein at least 5 amino acids of amino acid sequence set forth as SEQ ID NO: 10 are modified. In some embodiments, the heavy chain comprises an amino acid sequence wherein at least 6 amino acids of amino acid sequence set forth as SEQ ID NO: 10 are modified. In some embodiments, the heavy chain comprises an amino acid sequence wherein at least 7 amino acids of amino acid sequence set forth as SEQ ID NO: 10 are modified. In some embodiments, the heavy chain comprises an amino acid sequence wherein at least 8 amino acids of amino acid sequence set forth as SEQ ID NO: 10 are modified. In some embodiments, the heavy chain comprises an amino acid sequence wherein at least 9 amino acids of amino acid sequence set forth as SEQ ID NO: 10 are modified. In some embodiments, the heavy chain comprises an amino acid sequence wherein at least 10 amino acids of amino acid sequence set forth as SEQ ID NO: 10 are modified.

MICA/B Antibody Complementarily Determining Regions

Disclosed herein are antibodies that specifically bind to MICA/B having a light chain comprising a light chain complementarity determining region (CDR). In some embodiments, antibodies binding to MICA/B comprise at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, and a light chain CDR3 having an amino acid sequence at least about 70% identical to an amino acid sequence set forth as SEQ ID NO: 3. In some embodiments, antibodies binding to MICA/B comprise at least one of a light chain a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, and a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3. In some embodiments, antibodies binding to MICA/B comprise at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, and a light chain CDR3 having an amino acid sequence 100% identical to an amino acid sequence set forth as SEQ ID NO: 3.

Further disclosed herein are antibodies that specifically bind to MICA/B having a heavy chain comprising a heavy chain complementarity determining region (CDR). In some embodiments, antibodies binding to MICA/B comprise at least one of a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, a heavy chain CDR3 having an amino acid sequence at least about 70% identical to an amino acid sequence set forth as SEQ ID NO: 6. In some embodiments, antibodies binding to MICA/B comprise at least one of a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to MICA/B comprise at least one of a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, a heavy chain CDR3 having an amino acid sequence 100% identical to an amino acid sequence set forth as SEQ ID NO: 6.

Also disclosed herein are antibodies binding to MICA/B comprising a light chain complementarity determining region (CDR) and a heavy chain complementarity determining region (CDR). In some embodiments, antibodies binding to MICA/B comprise at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, a light chain CDR3 having an amino acid sequence at least about 70% identical to an amino acid sequence set forth as SEQ ID NO: 3, a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, and a heavy chain CDR3 having an amino acid sequence at least about 70% identical to an amino acid sequence set forth as SEQ ID NO: 6. In some embodiments, antibodies binding to MICA/B comprise at least one of a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3, a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, and a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to MICA/B comprise at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, a light chain CDR3 having an amino acid sequence 100% identical to an amino acid sequence set forth as SEQ ID NO: 3, a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, and a heavy chain CDR3 having an amino acid sequence 100% identical to an amino acid sequence set forth as SEQ ID NO: 6.

METHODS OF TREATMENT AND USE

Provided herein are methods of treating cancer (e.g. hepatocellular carcinoma) in an individual in need thereof comprising administration of an MICA/B antibody disclosed herein.

Further provided herein are methods of reducing level of soluble MICA/B proteins in an individual in need thereof comprising administration of an MICA/B antibody disclosed herein.

In some embodiments, antibodies binding to MICA/B comprise at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, and a light chain CDR3 having an amino acid sequence at least about 70% identical to an amino acid sequence set forth as SEQ ID NO: 3. In some embodiments, antibodies binding to MICA/B comprise at least one of a light chain a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, and a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3. In some embodiments, antibodies binding to MICA/B comprise at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, and a light chain CDR3 having an amino acid sequence 100% identical to an amino acid sequence set forth as SEQ ID NO: 3.

Further disclosed herein are antibodies that specifically bind to MICA/B having a heavy chain comprising a heavy chain complementarity determining region (CDR). In some embodiments, antibodies binding to MICA/B comprise at least one of a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, a heavy chain CDR3 having an amino acid sequence at least about 70% identical to an amino acid sequence set forth as SEQ ID NO: 6. In some embodiments, antibodies binding to MICA/B comprise at least one of a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to MICA/B comprise at least one of a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, a heavy chain CDR3 having an amino acid sequence 100% identical to an amino acid sequence set forth as SEQ ID NO: 6.

Also disclosed herein are antibodies binding to MICA/B comprising a light chain complementarity determining region (CDR) and a heavy chain complementarity determining region (CDR). In some embodiments, antibodies binding to MICA/B comprise at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, a light chain CDR3 having an amino acid sequence at least about 70% identical to an amino acid sequence set forth as SEQ ID NO: 3, a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, and a heavy chain CDR3 having an amino acid sequence at least about 70% identical to an amino acid sequence set forth as SEQ ID NO: 6. In some embodiments, antibodies binding to MICA/B comprise at least one of a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3, a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, and a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to MICA/B comprise at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, a light chain CDR3 having an amino acid sequence 100% identical to an amino acid sequence set forth as SEQ ID NO: 3, a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO:

5, and a heavy chain CDR3 having an amino acid sequence 100% identical to an amino acid sequence set forth as SEQ ID NO: 6.

Disclosed herein are antibodies that specifically bind to MICA/B having a light chain comprising a light chain variable domain (VL). In some embodiments, antibodies binding to MICA/B comprise a light chain variable domain (VL) having an amino acid sequence at least about 70% identical to an amino acid sequence set forth as SEQ ID NO: 7. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7. In some embodiments, the VL has an amino acid sequence 100% identical to an amino acid sequence set forth as SEQ ID NO: 7.

Further disclosed herein are antibodies that specifically bind to MICA/B having a heavy chain comprising a heavy chain variable domain (VH). In some embodiments, antibodies binding to MICA/B comprise a heavy chain variable domain (VH) having an amino acid sequence at least about 70% identical to an amino acid sequence set forth as SEQ ID NO: 8. In some embodiments the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8. In some embodiments, the VH has an amino acid sequence 100% identical to an amino acid sequence set forth as SEQ ID NO: 8.

Also disclosed herein are antibodies binding to MICA/B comprising a light chain variable domain (VL) and a heavy chain variable domain (VH). In some embodiments, antibodies binding to MICA/B comprise a light chain variable domain (VL) having an amino acid sequence at least about 70% identical to an amino acid sequence set forth as SEQ ID NO: 7 and a heavy chain variable domain (VH) having an amino acid sequence at least about 70% identical to an amino acid sequence set forth as SEQ ID NO: 8. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8. In some embodiments, the VL has an amino acid sequence 100% identical to an amino acid sequence set forth as SEQ ID NO: 7 and the VH has an amino acid sequence 100% identical to an amino acid sequence set forth as SEQ ID NO: 8.

In some embodiments, the antibodies specifically bind to a MICA protein. In some embodiments, the antibodies specifically bind to a MICB protein. In some embodiments, the antibodies specifically bind to both MICA and MICB protein. In some embodiments, the antibodies bind to an alpha-3 domain of a MICA protein. In some embodiments, the antibodies bind to an alpha-3 domain of a MICB protein. In some embodiments, the antibodies bind to an alpha-3 domain of both MICA and MICB protein. In some embodiments, the antibodies bind to a MICA protein that is membrane-bound MICA protein. In some embodiments, the antibodies bind to a MICA protein that is soluble MICA protein. In some embodiments, the antibodies bind to a MICA protein that is both membrane-bound MICA protein and soluble MICA protein. In some embodiments, the antibodies bind to a MICB protein that is membrane-bound MICB protein. In some embodiments, the antibodies bind to a MICB protein that is soluble MICB protein. In some embodiments, the antibodies bind to a MICB protein that is both membrane-bound MICB protein and soluble MICB protein.

In some embodiments, antibodies that specifically bind to MICA/B are monoclonal antibodies. In some embodiments, the antibody is an antigen binding fragment. In some embodiments, the antibody is selected from a whole immunoglobulin, an scFv, a Fab, a F(ab')2, or a disulfide linked Fv. In some embodiments, the antibody is an IgG or an IgM. In some embodiments, the antibody is humanized. In some embodiments, the antibody is chimeric.

In some embodiments, the antibodies disclosed herein reduce level of soluble MICA protein. In some embodiments, the antibodies disclosed herein reduce level of soluble MICB protein. In some embodiments, the antibodies disclosed herein reduce level of both soluble MICA protein and soluble MICB protein. In some embodiments, the antibodies disclosed herein reduce shedding of soluble MICA protein. In some embodiments, the antibodies disclosed herein reduce shedding of soluble MICB protein. In some embodiments, the antibodies disclosed herein reduce shedding of both soluble MICA protein and soluble MICB protein. In some embodiments, the antibodies disclosed herein inhibit shedding of soluble MICA protein. In some embodiments, the antibodies disclosed herein inhibit shedding of soluble MICB protein. In some embodiments, the antibodies disclosed herein inhibit shedding of both soluble MICA protein and soluble MICB protein. In some embodiments, the antibodies disclosed herein reduce or inhibit shedding of soluble MICA protein, soluble MICB protein, or both, thereby reducing level of soluble MICA protein, soluble MICB protein, or both.

Any suitable route of administration is contemplated for use with the methods disclosed herein. In some embodiments, the antibody is administered by intravenous administration. In some embodiments, the antibody is administered by subcutaneous administration. In some embodiments, the antibody is administered locally. In some embodiments, the antibody is administered systemically (e.g., intravenously, intramuscularly, subcutaneously, intradermally, orally, intranasally, sublingually). In some embodiments, the antibody is formulated as a salve, lotion or emulsion. In some embodiments, the antibody is formulated as a solution. In some embodiments, the antibody is formulated for topical, oral, buccal, or nasal administration.

In some embodiments, the individual is monitored prior to administration of the antibody. Symptoms are identified and their severity is assessed. An antibody as described herein is administered alone or in combination with additional treatments, singly or multiply over time as discussed herein or known to one of skill in the art. In some embodiments, the individual is monitored such that the efficacy of the treatment regimen is determined. In some embodiments, a treatment regimen is modified in response to preliminary treatment outcomes, such that treatment dose or frequency or dose and frequency is altered so as to attain a desired level of subject response in light of symptom alleviation, side effect reduction, or a combination of symptom alleviation and side effect reduction.

Therapeutically effective amounts or dosages are contemplated to include dosages of about 0.01 mg/kg to about 20 mg/kg, about for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.1 mg/kg, about 3.2 mg/kg, about 3.3 mg/kg, about 3.4 mg/kg, about 3.5 mg/kg, about 3.6 mg/kg, about 3.7 mg/kg, about 3.8 mg/kg, about 3.9 mg/kg, about 4 mg/kg, about 4.1 mg/kg, about 4.2 mg/kg, about 4.3 mg/kg, about 4.4 mg/kg, about 4.5 mg/kg, about 4.6 mg/kg, about 4.7 mg/kg, about 4.8 mg/kg, about 4.9 mg/kg, about 5 mg/kg, about 5.1 mg/kg, about 5.2 mg/kg, about 5.3 mg/kg, about 5.4 mg/kg, about 5.5 mg/kg, about 5.6 mg/kg, about 5.7 mg/kg, about 5.8 mg/kg, about 5.9 mg/kg, about 6 mg/kg, about 6.1 mg/kg, about 6.2 mg/kg, about 6.3 mg/kg, about 6.4 mg/kg, about 6.5 mg/kg, about 6.6 mg/kg, about 6.7 mg/kg, about 6.8 mg/kg, about 6.9 mg/kg, about 7 mg/kg, about 7.1 mg/kg, about 7.2 mg/kg, about 7.3 mg/kg, about 7.4 mg/kg, about 7.5 mg/kg, about 7.6 mg/kg, about 7.7 mg/kg, about 7.8 mg/kg, about 7.9 mg/kg, about 8 mg/kg, about 8.1 mg/kg, about 8.2 mg/kg, about 8.3 mg/kg, about 8.4 mg/kg, about 8.5 mg/kg, about 8.6 mg/kg, about 8.7 mg/kg, about 8.8 mg/kg, about 8.9 mg/kg, about 9 mg/kg, about 9.1 mg/kg, about 9.2 mg/kg, about 9.3 mg/kg, about 9.4 mg/kg, about 9.5 mg/kg, about 9.6 mg/kg, about 9.7 mg/kg, about 9.8 mg/kg, about 9.9 mg/kg, about 10 mg/kg, about 10.1 mg/kg, about 10.2 mg/kg, about 10.3 mg/kg, about 10.4 mg/kg, about 10.5 mg/kg, about 10.6 mg/kg, about 10.7 mg/kg, about 10.8 mg/kg, about 10.9 mg/kg, about 11 mg/kg, about 11.1 mg/kg, about 11.2 mg/kg, about 11.3 mg/kg, about 11.4 mg/kg, about 11.5 mg/kg, about 11.6 mg/kg, about 11.7 mg/kg, about 11.8 mg/kg, about 11.9 mg/kg, about 12 mg/kg, about 12.1 mg/kg, about 12.2 mg/kg, about 12.3 mg/kg, about 12.4 mg/kg, about 12.5 mg/kg, about 12.6 mg/kg, about 12.7 mg/kg, about 12.8 mg/kg, about 12.9 mg/kg, about 13 mg/kg, about 13.1 mg/kg, about 13.2 mg/kg, about 13.3 mg/kg, about 13.4 mg/kg, about 13.5 mg/kg, about 13.6 mg/kg, about 13.7 mg/kg, about 13.8 mg/kg, about 13.9 mg/kg, about 14 mg/kg, about 14.1 mg/kg, about 14.2 mg/kg, about 14.3 mg/kg, about 14.4 mg/kg, about 14.5 mg/kg, about 14.6 mg/kg, about 14.7 mg/kg, about 14.8 mg/kg, about 14.9 mg/kg, about 15 mg/kg, about 15.1 mg/kg, about 15.2 mg/kg, about 15.3 mg/kg, about 15.4 mg/kg, about 15.5 mg/kg, about 15.6 mg/kg, about 15.7 mg/kg, about 15.8 mg/kg, about 15.9 mg/kg, about 16 mg/kg, about 16.1 mg/kg, about 16.2 mg/kg, about 16.3 mg/kg, about 16.4 mg/kg, about 16.5 mg/kg, about 16.6 mg/kg, about 16.7 mg/kg, about 16.8 mg/kg, about 16.9 mg/kg, about 17 mg/kg, about 17.1 mg/kg, about 17.2 mg/kg, about 17.3 mg/kg, about 17.4 mg/kg, about 17.5 mg/kg, about 17.6 mg/kg, about 17.7 mg/kg, about 17.8 mg/kg, about 17.9 mg/kg, about 18 mg/kg, about 18.1 mg/kg, about 18.2 mg/kg, about 18.3 mg/kg, about 18.4 mg/kg, about 18.5 mg/kg, about 18.6 mg/kg, about 18.7 mg/kg, about 18.8 mg/kg, about 18.9 mg/kg, about 19 mg/kg, about 19.1 mg/kg, about 19.2 mg/kg, about 19.3 mg/kg, about 19.4 mg/kg, about 19.5 mg/kg, about 19.6 mg/kg, about 19.7 mg/kg, about 19.8 mg/kg, about 19.9 mg/kg, about or 20 mg/kg. Therapeutically effective amounts or dosages, in some cases, are contemplated to include dosages of about 0.1 mg/kg to about 2.0 mg/kg.

Methods of treatment herein comprise one or more administrations of MICA/B antibodies in doses disclosed herein. In some embodiments, methods comprise one administration of MICA/B antibodies. In some embodiments, methods comprise two administrations of MICA/B antibodies. In some embodiments, methods comprise three administrations of MICA/B antibodies. In some embodiments, methods comprise four administrations of MICA/B antibodies. In some embodiments, methods comprise five administrations of MICA/B antibodies. In some embodiments, methods comprise six administrations of MICA/B antibodies. In some embodiments, one or more administrations of MICA/B antibodies are administered daily. In some embodiments, one or more administrations of MICA/B antibodies are administered weekly. In some embodiments, one or more administrations of MICA/B antibodies are administered biweekly. In some embodiments, one or more administrations of MICA/B antibodies are administered monthly. In some embodiments, one or more administrations of MICA/B antibodies are administered every three months. In some embodiments, one or more administrations of MICA/B antibodies are administered every six months. In some embodiments, one or more administrations of MICA/B antibodies are administered yearly.

Pharmaceutical Compositions

Also disclosed herein are pharmaceutical compositions comprising MICA/B antibodies disclosed herein and a pharmaceutically acceptable carrier or excipient.

In some embodiments, excipients for use with the compositions disclosed herein include maleic acid, tartaric acid, lactic acid, citric acid, acetic acid, sodium bicarbonate, sodium phosphate, histidine, glycine, sodium chloride, potassium chloride, calcium chloride, zinc chloride, water, dextrose, N-methylpyrrolidone, dimethyl sulfoxide, N,N-dimethylacetamide, ethanol, propylene glycol, polyethylene glycol, diethylene glycol monoethyl ether, and surfactant polyoxyethylene-sorbitan monooleate.

In some embodiments, the compositions further comprise an additional therapeutic agent. In some embodiments, the therapeutic agent is a chemotherapeutic agent. The chemotherapeutic agents can include, among others, cytotoxic agents, anti-metabolite agents (e.g., folate antagonists, purine analogs, pyrimidine analogs, etc.), topoisomerase inhibitors (e.g., camptothecin derivatives, anthracenedione, anthracyclines, epipodophyllotoxins, quinoline alkaloids, etc.), anti-microtubule agents (e.g., taxanes, vinca alkaloids), protein synthesis inhibitors (e.g., cephalotaxine, camptothecin derivatives, quinoline alkaloids), alkylating agents (e.g., alkyl sulfonates, ethylenimines, nitrogen mustards, nitrosoureas, platinum derivatives, triazenes, etc.), alkaloids, terpenoids, and kinase inhibitors.

In some embodiments, the antibody and the therapeutic agent are in the same formulation. In some embodiments, the antibody and the therapeutic agent are in different formulation. In some embodiments, antibody described herein is used prior to the administration of the other therapeutic agent. In some embodiments, antibody described herein is used concurrently with the administration of the other therapeutic agent. In some embodiments, antibody described herein is used subsequent to the administration of the other therapeutic agent.

Pharmaceutical formulations, in some embodiments, are made to be compatible with a particular local, regional or systemic administration or delivery route. Thus, pharmaceutical formulations include carriers, diluents, or excipients suitable for administration by particular routes. Specific non-limiting examples of routes of administration for compositions herein are parenteral, e.g., intravenous, intra-arterial, intradermal, intramuscular, subcutaneous, intra-pleural, transdermal (topical), transmucosal, intra-cranial, intra-spinal, intra-ocular, rectal, oral (alimentary), mucosal administration, and any other formulation suitable for the treatment method or administration protocol.

In some embodiments, solutions or suspensions used for parenteral application include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates; and agents for the adjustment of tonicity such as sodium chloride or dextrose. In some embodiments, pH is adjusted with acids or bases, such as hydrochloric acid or sodium hydroxide.

Pharmaceutical formulations for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In some embodiments, the carrier is a solvent or dispersion medium containing, for example, water, ethanol, polyol (for example, glycerol, propylene glycol, and liquid polyetheylene glycol, and the like), or suitable mixtures thereof. Fluidity is maintained, in some embodiments, for example, by the use of a coating such as lecithin, by the maintenance of the required particle size in the case of dispersion, and by the use of surfactants. Antibacterial and antifungal agents include, for example, parabens, chlorobutanol, phenol, ascorbic acid, and thimerosal. Isotonic agents, for example, sugars; polyalcohols such as mannitol or sorbitol; or sodium chloride, in some embodiments, are included in the composition. In some cases, also included is an agent which delays absorption, in some embodiments, for example, aluminum monostearate or gelatin prolongs absorption of injectable compositions.

In some embodiments, sterile injectable formulations are prepared by incorporating the active composition in the required amount in an appropriate solvent with one or a combination of above ingredients. Generally, dispersions are prepared by incorporating the active composition into a sterile vehicle containing a basic dispersion medium and any other ingredient. In the case of sterile powders for the preparation of sterile injectable solutions, methods of preparation include, for example, vacuum drying and freeze-drying which yields a powder of the active ingredient plus any additional desired ingredient from a previously prepared solution thereof.

For transmucosal or transdermal administration, penetrants appropriate to the barrier to be permeated are used in the formulation. Such penetrants are known in the art, and include, for example, for transmucosal administration, detergents, bile salts, and fusidic acid derivatives. In some embodiments, transmucosal administration is accomplished through the use of nasal sprays, inhalation devices (e.g., aspirators) or suppositories. For transdermal administration, the active compounds are formulated into ointments, salves, gels, creams or patches.

In some embodiments, the pharmaceutical formulations are prepared with carriers that protect against rapid elimination from the body, such as a controlled release formulation or a time delay material such as glyceryl monostearate or glyceryl stearate. The formulations, in some embodiments, are also delivered using articles of manufacture such as implants and microencapsulated delivery systems to achieve local, regional or systemic delivery or controlled or sustained release.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: MICA/B Monoclonal Antibody Generation and Screening

The antibodies are prepared using conventional techniques known in the art, for example, Kohler and Milstein, 1975, Nature 256(5517):495-7; Coligan et al., supra, sections 2.5.1-2.6.7; Current Protocols in Immunology, John Wiley & Sons, Inc. (1992); and Antibodies: A Laboratory Manual, Harlow and Lane, eds., Cold Spring Harbor Press, New York (1988); Monoclonal Antibodies: Methods and Protocols in Methods Mol Biol., Vol. 378, Albitar M., ed., Humana Press (2007), which are hereby incorporated herein by reference. Monoclonal antibodies are generated in mice by administration of the immunogen and subsequent isolation of B-cells that make antibodies. The B-cells are then immortalized by fusion to another, stable cell type of the same species of the B-cell to create a hybridoma. The hybridoma clones are screened using ELISA for their ability to bind the antigen (MICA/B). An individual B-cell makes one specific antibody (i.e., is clonally monospecific) which is defined by its primary amino acid sequence and its underlying gene sequence. Monoclonal antibodies showing specific binding to MICA/B are isolated and purified from hybridoma cultures using conventional methodology such as affinity chromatography with Protein-A Sepharose, size-exclusion chromatography, and ion-exchange chromatography (see, e.g., Coligan, et al., supra, sections 2.7.1-2.7.12 and sections 2.9.1-2.9.3; Barnes, et al., Purification of Immunoglobulin G (IgG), in Methods Mol. Biol., Vol. 10, pages 79-104, Humana Press (1992)).

Example 2: PDI-1 Antibody Binding Kinetics Measurement

Affinity kinetics was determined on a ForteBio Octet Red96 analyzer. Briefly, PDI-1 (30 μg/ml) was captured on Dip and Read™ Anti-mouse IgG Fc Capture (AMC) Biosensors (ForteBio) at room temperature in an assay buffer of PBS+0.1% BSA+0.02% Tween-20 (pH 7.2). Sensors were washed in assay buffer and then incubated with purified 6×His-MICA*08 and 6×His-MICA*01 proteins (100 nM), respectively, in 2-fold dilution series for 5 minutes in assay buffer to determine association kinetics of the antibody with the protein antigen. Sensors were then incubated in assay buffer for 10 minutes to determine dissociation kinetics. The resulting kinetics parameters were calculated with ForteBio analysis suite 8.0 using a 1:1 model. Results for these assays are shown in FIG. 1.

Example 3: PDI-1 Antibody Binding to MICA/B Alleles

Figure 2:
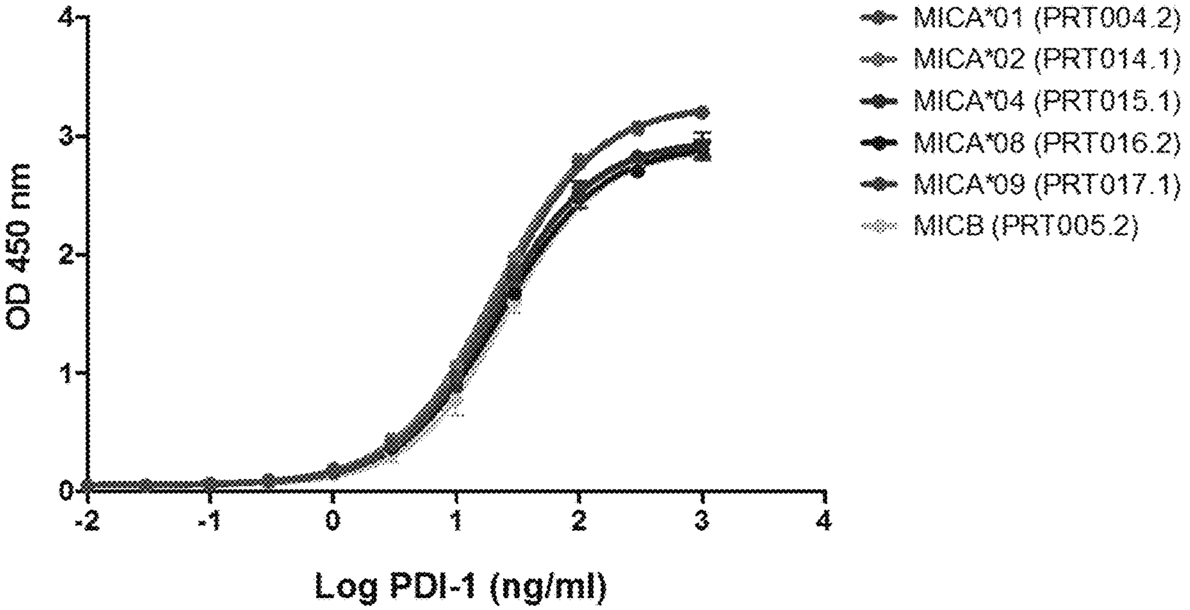
FIG. 2 exemplifies binding of antibody PDI-1 to MICA/B alleles by ELISA.

Recombinant MICA*01, MICA*02, MICA*04, MICA*08, MICA*09, and MICB proteins were diluted to 1 μg/ml in 50 mM sodium carbonate buffer, pH 9.6, and coated onto high binding 96-well microplates (Corning #9018), 100 ng in 100 ul per well. The following morning, coated ELISA plates were washed three times with TBS-Tween-20, pH 7.4 and then blocked in SuperBlock T20 Blocking Buffer (Pierce #37536). After blocking, ELISA plates were washed once with TBS-T and incubated with serially diluted PDI-1 antibody (0-1 μg/ml) for approximately two hours at room temperature. Following the incubation, ELISA plates were washed three times with TBS-T and then incubated with Goat anti-Mouse IgG (H+L)-HRP conjugate (ThermoFisher Scientific #626520) for 45 minutes at room temperature with shaking (~400 rpm). After the incubation, ELISA plates were washed three times with TBS-T and incubated with Super Sensitive Liquid Substrate TMB (Sigma #T4444), 100 ul per well, until color development was sufficient. The reaction was stopped with 1N sulfuric acid, 100 ul per well. Optical density (OD) values were measured at 450 nm using a microplate reader. The result of this assay is shown in FIG. 2.

Example 4: PDI-1 Antibody Binding to Cell Surface MICA

Figure 3:
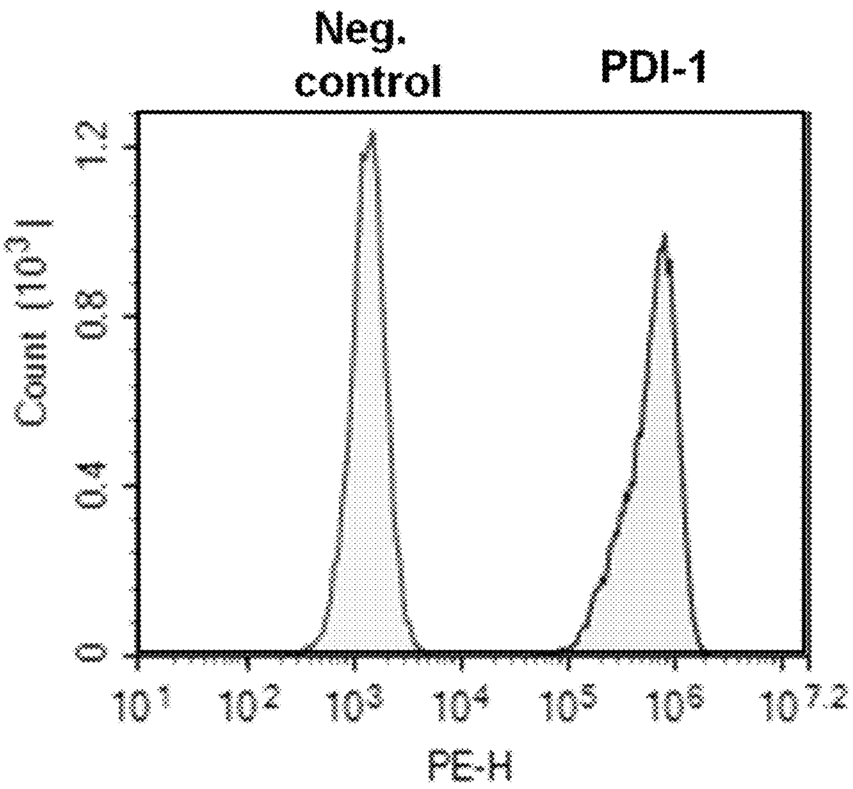
FIG. 3 exemplifies antibody PDI-1 binds to cell surface MICA, evaluated by cell staining of TRAMP C2 cell transfected with MICA*04.

Mouse prostate adenocarcinoma TRAMP-C2 cells (TC2) (ATCC, Manassas, VA) was used to generate a stable cell line expressing MICA*04 allele (TC2-MICA-04). Binding of PDI-1 to TC2-MICA-04 was analyzed by flow cytometry. Briefly, cells were first stained with LIVE/DEAD Near IR Stain (Thermo) for 30 min at 4° C., and then washed once by centrifugation with FACS Buffer (1 mM EDTA, 25 mM HEPES, 2% FBS in 1×PBS). About 2-3×$10^5$ TC2-MICA-04 cells were incubated with 100 μl of FACS Buffer containing 500 ng PDI-1 antibody at 4° C. for 30 min, followed by incubation with 100 μl 2 μg/ml PE conjugated goat-anti-mouse IgG (Biolegend, San Diego, CA) secondary Ab at 4° C. for 30 min. Cells were then washed once and cell pellet resuspended with FACS Buffer for FACS analysis gated on live cells. Significantly higher PE fluorescence signal was observed with TC2-MICA-04 cells compared to parental TC2 cells indicated binding of PDI-1 to surface expressed MICA. Result for this assay is shown in FIG. 3.

Example 5: PDI-1 Antibody Inhibits MICA Shedding From PLC/PRF/5 Cells

Figure 4:
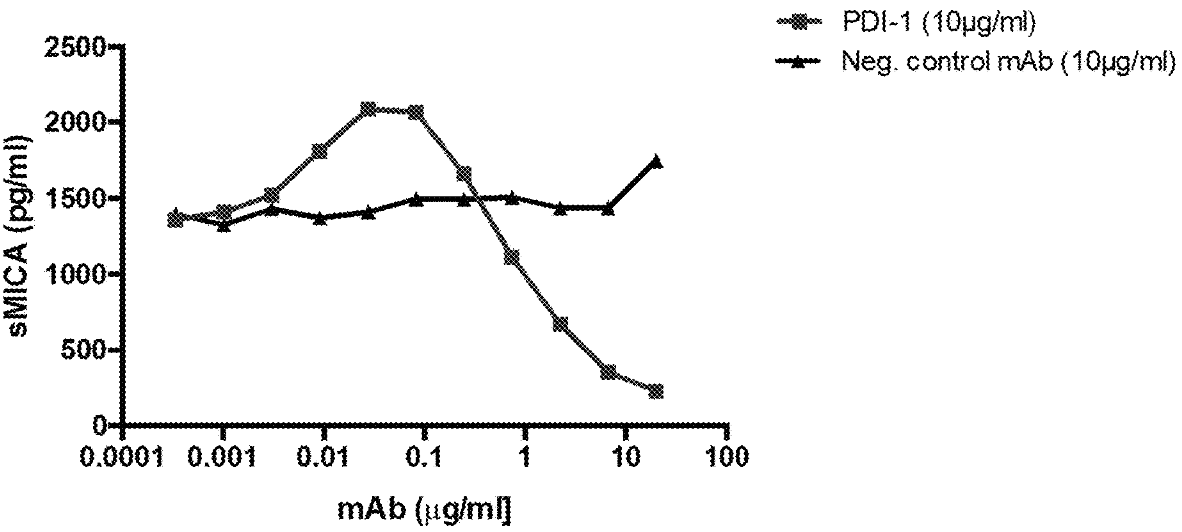
FIG. 4 exemplifies antibody PDI-1 inhibits MICA shedding from PLC/PRF/5 cells.

4×$10^4$ PLC/PRF/5 cells (Hepatocellular Carcinoma) (ATCC, Manassas, VA) were plated in 96-well plate and incubated at 37° C. overnight. Cells were then treated with 100 μl Complete Media (MEM+10% FBS, Thermo, Grand Island, NY) containing PDI-1 and negative control antibodies, respectively, and incubated at 37° C. for another day. Cell supernatants containing shed MICA were used to determine the level of soluble MICA by ELISA. Briefly, 96-well plate was coated with 100 μl 2 μg/ml capture Ab anti-human MICA/MICB, clone 6D4 (Biolegend, San Diego, CA) overnight at 4° C. Plate was blocked and then incubated with cell supernatants and MICA standards for 2 hours. After incubation, plates were washed and followed by 1 hour incubation with 100 μl 500 ng/ml detection Ab (anti-human-MICA mAb, clone 159227, R&D Systems, Minneapolis, MN) conjugated with biotin. Next, 100 μl HRP conjugated streptavidin (HRP-SA) (R&D Systems, Minneapolis, MN) was added to wells and incubated for 30 min. Samples were developed with TMB for 4 min, stopped with 1N sulfuric acid and detected with absorbance at 450 nm. Soluble MICA level was interpolated from standard curve. Result for this assay is shown in FIG. 4.

Figure 5:
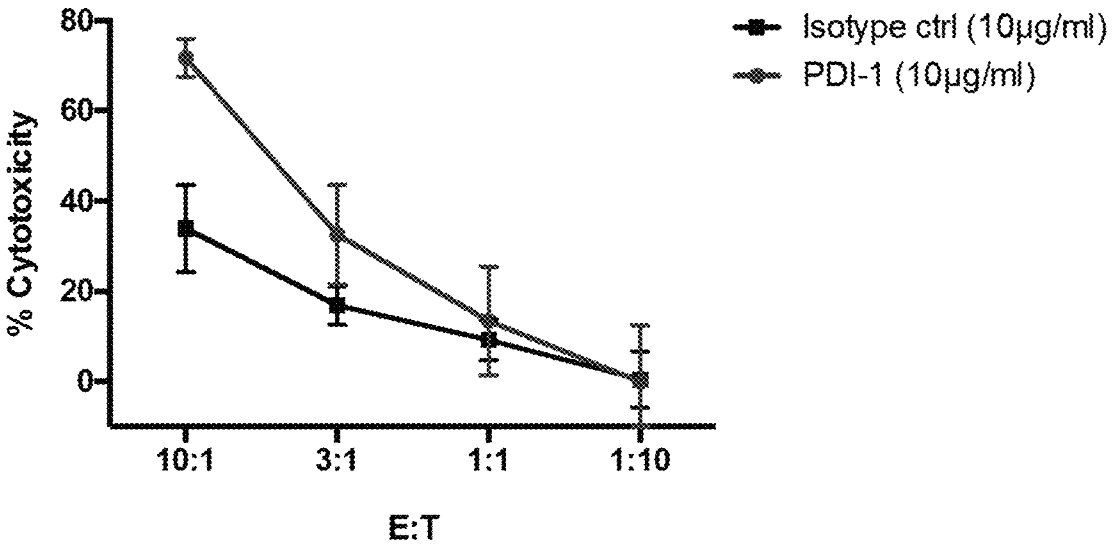
FIG. 5 exemplifies PDI-1 enhances NK-92 cells mediated cytotoxicity of PLC/PRF/5 cells.

Example 6: PDI-1 Antibody Enhances NK-92 Cells Mediated Cytotoxicity to PLC/PRF/5 Cells PLC/PRF/5 (Target) cells were suspended in RPMI-1640 with 10% FBS, and plated into 96-well flat bottom plates (Costar) at 6000 cells/well. Cells were then incubated with PDI-1 antibody (10 μg/ml) for 24 hours before being labeled with calcein AM (1 μM) for 3 hours at 37° C., 5% $CO_2$. Wells were washed, and NK-92 cells (Effector) suspended in RPMI-1640 with 10% FBS were then added to wells at various Effector-to-Target (E:T) ratios as indicated and cocultured with target cells for 4 hours. At the end of the cultures, the supernatant was removed, replaced with PBS, and the calcein AM signal was measured using an VICTOR Multilabel plate reader (Perkin Elmer). An isotype matched nonreactive immunoglobulin (R&D) antibody was used as a control. Result for this assay is shown in FIG. 5.

Figure 6:
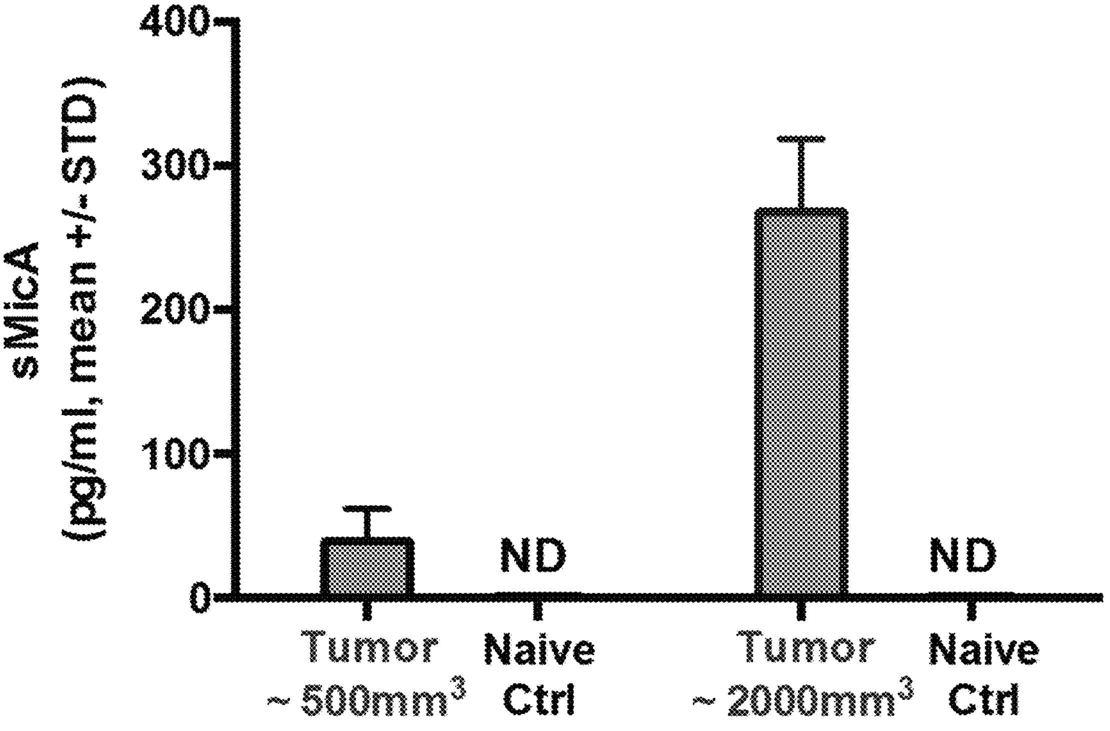
FIG. 6 exemplifies measurement of soluble MICA levels in the serum of human liver cancer xenograft model using PDI-1 antibody.

Example 7: Soluble MICA Sandwich ELISA 96-well high binding plates (Costar #9018) were coated overnight at 4° C. with 200 ng/well anti-MICA capture antibody in sodium carbonate buffer (50 mM pH 9.6) in 100 μl volume, then blocked with SuperBlock T20 (Pierce #37536) and washed with TBS-T. Next, serum samples from human liver cancer xenograft model diluted 1:3 in SuperBlock T20 or recombinant MICA*08 standard were added to the plate and incubated for 2 hours at RT. After 2 hours incubation, the plate was washed three times with TBS-T and then incubated with biotinylated PDI-1 detection antibody diluted to 1 μg/ml in SuperBlock T20. After 1 hour incubation, the plate was washed three times with TBS-T, and then incubated for 45 minutes with Streptavidin-HRP conjugate (Invitrogen #SNN2004) 1/5000 dilution in SuperBlock T20, 100 μl per well. After 45 minutes incubation, the plate was washed three times with TBS-T. Next, Supersensitive Liquid Substrate TMB for ELISA (Sigma T4444), 100 μl per well, was added and color was allowed to develop. The reaction was stopped by adding 100 μl per well 1N $H_2SO_4$. Output was measured by O.D. determined at 450 nm. The result of this assay is shown in FIG. 6.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed. It is intended that the following claims define the scope of the invention and that methods and structures within the scope of these claims and their equivalents be covered thereby.

SEQUENCE LISTING

```
Sequence total quantity: 11
SEQ ID NO: 1            moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 1
SASQGISNYL N                                                        11

SEQ ID NO: 2            moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 2
TSLLHSG                                                             7

SEQ ID NO: 3            moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 3
QQYSKFPRT                                                           9

SEQ ID NO: 4            moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 4
GYTFTNYGMN                                                          10

SEQ ID NO: 5            moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 5
INTYTGEPTY ADDFKG                                                   16

SEQ ID NO: 6            moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 6
NYGNYLFDY                                                           9

SEQ ID NO: 7            moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 7
DIQMTQTTSS LSASLGDRVT ISCSASQGIS NYLNWYQQKP DGTLKLLIQY TSLLHSGVPS  60
RFSGSGSGTE YSLTISNLEP EDIATYFCQQ YSKFPRTFGG GTKLEIKR                108

SEQ ID NO: 8            moltype = AA  length = 118
FEATURE                 Location/Qualifiers
REGION                  1..118
                        note = Description of Artificial Sequence: Synthetic
                         polypeptide
```

-continued

```
source                1..118
                      mol_type = protein
                      organism = synthetic construct
SEQUENCE: 8
QIQLVQSGPE LKKSGETVKI SCKAFGYTFT NYGMNWVKQA PGKGLKWMGW INTYTGEPTY  60
ADDFKGRFAF SLETSASTAY LQINHLKNED TATYFCARNY GNYLFDYWGQ GTTLTVSS    118

SEQ ID NO: 9          moltype = AA  length = 234
FEATURE               Location/Qualifiers
REGION                1..234
                      note = Description of Artificial Sequence: Synthetic
                       polypeptide
source                1..234
                      mol_type = protein
                      organism = synthetic construct
SEQUENCE: 9
METDTLLLWV LLLWVPGSTG DIQMTQTTSS LSASLGDRVT ISCSASQGIS NYLNWYQQKP  60
DGTLKLLIQY TSLLHSGVPS RFSGSGSGTE YSLTISNLEP EDIATYFCQQ YSKFPRTFGG  120
GTKLEIKRAD AAPTVSIFPP SSEQLTSGGA SVVCFLNNFY PKDINVKWKI DGSERQNGVL  180
NSWTDQDSKD STYSMSSTLT LTKDEYERHN SYTCEATHKT STSPIVKSFN RNEC        234

SEQ ID NO: 10         moltype = AA  length = 467
FEATURE               Location/Qualifiers
REGION                1..467
                      note = Description of Artificial Sequence: Synthetic
                       polypeptide
source                1..467
                      mol_type = protein
                      organism = synthetic construct
SEQUENCE: 10
METDTLLLWV LLLWVPGSTG QIQLVQSGPE LKKSGETVKI SCKAFGYTFT NYGMNWVKQA  60
PGKGLKWMGW INTYTGEPTY ADDFKGRFAF SLETSASTAY LQINHLKNED TATYFCARNY  120
GNYLFDYWGQ GTTLTVSSAK TTAPSVYPLA PVCGDTTGSS VTLGCLVKGY FPEPVTLTWN  180
SGSLSSGVHT FPAVLQSDLY TLSSSVTVTS STWPSQSITC NVAHPASSTK VDKKIEPRGP  240
TIKPCPPCKC PAPNLLGGPS VFIFPPKIKD VLMISLSPIV TCVVVDVSED DPDVQISWFV  300
NNVEVHTAQT QTHREDYNST LRVVSALPIQ HQDWMSGKEF KCKVNNKDLP APIERTISKP  360
KGSVRAPQVY VLPPPEEEMT KKQVTLTCMV TDFMPEDIYV EWTNNGKTEL NYKNTEPVLD  420
SDGSYFMYSK LRVEKKNWVE RNSYSCSVVH EGLHNHHTTK SFSRTPG                467

SEQ ID NO: 11         moltype = AA  length = 6
FEATURE               Location/Qualifiers
REGION                1..6
                      note = Description of Artificial Sequence: Synthetic 6xHis
                       tag
source                1..6
                      mol_type = protein
                      organism = synthetic construct
SEQUENCE: 11
HHHHHH                                                             6
```

What is claimed is:

1. A monoclonal antibody or an antigen-binding fragment thereof that specifically binds to a MICA protein, a MICB protein, or both MICA and MICB proteins, comprising a light chain complementarity determining region 1 (CDR1) sequence comprising the amino acid sequence set forth as SEQ ID NO: 1, a light chain complementarity determining region 2 (CDR2) sequence comprising the amino acid sequence set forth as SEQ ID NO: 2, a light chain complementarity determining region 3 (CDR3) sequence comprising the amino acid sequence set forth as SEQ ID NO: 3, a heavy chain complementarity determining region 1 (CDR1) sequence comprising the amino acid sequence set forth as SEQ ID NO: 4, a heavy chain complementarity determining region 2 (CDR2) sequence comprising the amino acid sequence set forth as SEQ ID NO: 5, and a heavy chain complementarity determining region 3 (CDR3) sequence comprising the amino acid sequence set forth as SEQ ID NO: 6.

2. The monoclonal antibody of claim 1, wherein the monoclonal antibody or antigen-binding fragment thereof comprises a light chain variable domain (VL) comprising the amino acid sequence set forth as SEQ ID NO: 7.

3. The monoclonal antibody of claim 1, wherein the monoclonal antibody or antigen-binding fragment thereof comprises a heavy chain variable domain (VH) comprising the amino acid sequence set forth as SEQ ID NO: 8.

4. The monoclonal antibody of claim 1, wherein the monoclonal antibody or antigen-binding fragment thereof binds to alpha-3 domain of a MICA protein, a MICB protein, or both MICA and MICB proteins.

5. The monoclonal antibody of claim 1, wherein the MICA protein is a soluble MICA protein.

6. The monoclonal antibody of claim 1, wherein the MICB protein is a soluble MICB protein.

7. The monoclonal antibody of claim 1, wherein the monoclonal antibody or antigen-binding fragment thereof is selected from a whole immunoglobulin, an scFv, a Fab, a F(ab')2, or a disulfide linked Fv.

8. The monoclonal antibody of claim 1, wherein the monoclonal antibody or antigen-binding fragment thereof is an IgG or IgM.

9. The monoclonal antibody of claim 1, wherein the monoclonal antibody or fragment thereof is humanized or chimeric.

10. A pharmaceutical composition comprising a monoclonal antibody or an antigen-binding fragment thereof according to claim 1; and a pharmaceutically acceptable carrier or excipient.

11. A method of treating cancer in an individual in need thereof, comprising administering to the individual an effective amount of a monoclonal antibody or an antigen-binding fragment thereof that specifically binds to a MICA protein, a MICB protein, or both MICA and MICB proteins, comprising a light chain complementarity determining region 1 (CDR1) sequence comprising the amino acid sequence set forth as SEQ ID NO: 1, a light chain complementarity determining region 2 (CDR2) sequence comprising the amino acid sequence set forth as SEQ ID NO: 2, a light chain complementarity determining region 3 (CDR3) sequence comprising the amino acid sequence set forth as SEQ ID NO: 3, a heavy chain complementarity determining region 1 (CDR1) sequence comprising the amino acid sequence set forth as SEQ ID NO: 4, a heavy chain complementarity determining region 2 (CDR2) sequence comprising the amino acid sequence set forth as SEQ ID NO: 5, and a heavy chain complementarity determining region 3 (CDR3) sequence comprising the amino acid sequence set forth as SEQ ID NO: 6.

12. A method of reducing level of soluble MICA protein, soluble MICB protein, or both in an individual in need thereof, comprising administering to the individual an effective amount of a monoclonal antibody or an antigen-binding fragment thereof that specifically binds to a MICA protein, a MICB protein, or both MICA and MICB proteins, comprising of a light chain complementarity determining region 1 (CDR1) sequence comprising the amino acid sequence set forth as SEQ ID NO: 1, a light chain complementarity determining region 2 (CDR2) sequence comprising the amino acid sequence set forth as SEQ ID NO: 2, and a light chain complementarity determining region 3 (CDR3) sequence comprising the amino acid sequence set forth as SEQ ID NO: 3, a heavy chain complementarity determining region 1 (CDR1) sequence comprising the amino acid sequence set forth as SEQ ID NO: 4, a heavy chain complementarity determining region 2 (CDR2) sequence comprising the amino acid sequence set forth as SEQ ID NO: 5, and a heavy chain complementarity determining region 3 (CDR3) sequence comprising the amino acid sequence set forth as SEQ ID NO: 6.

* * * * *